US012637719B2

(12) United States Patent
Bouaboula et al.

(10) Patent No.: US 12,637,719 B2
(45) Date of Patent: May 26, 2026

(54) PANEL OF ER REGULATED GENES FOR USE IN MONITORING ENDOCRINE THERAPY IN BREAST CANCER

(71) Applicant: Sanofi, Paris (FR)

(72) Inventors: Monsif Bouaboula, Cambridge, MA (US); Hui Cao, Cambridge, MA (US); Joon Sang Lee, Cambridge, MA (US); Vasiliki Pelekanou, Cambridge, MA (US); Maysoun Shomali, Cambridge, MA (US)

(73) Assignee: SANOFI, Paris (FR)

( * ) Notice: Subject to any disclaimer, the term of this patent is extended or adjusted under 35 U.S.C. 154(b) by 453 days.

(21) Appl. No.: 18/253,640

(22) PCT Filed: Nov. 22, 2021

(86) PCT No.: PCT/US2021/060349

§ 371 (c)(1),
(2) Date: May 19, 2023

(87) PCT Pub. No.: WO2022/109395

PCT Pub. Date: May 27, 2022

(65) Prior Publication Data

US 2024/0002950 A1 Jan. 4, 2024

Related U.S. Application Data

(60) Provisional application No. 63/173,107, filed on Apr. 9, 2021, provisional application No. 63/117,229, filed on Nov. 23, 2020.

(30) Foreign Application Priority Data

Apr. 16, 2021 (EP) .................................... 21315066

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/158* (2013.01)

(58) Field of Classification Search
CPC ............ C12Q 1/6886; C12Q 2600/106; C12Q 2600/158; C12Q 2600/112; C12Q 2600/118
See application file for complete search history.

(56) References Cited

FOREIGN PATENT DOCUMENTS

WO 2012037410 A2 3/2012
WO 2014191726 A1 12/2014
(Continued)

OTHER PUBLICATIONS

Illumina, Inc, "HumanHT-12 v3 Expression BeadChip," Data Sheet found at https://www.illumina.com/Documents/products/datasheets/datasheet_humanht_12.pdf. pp. 1-3. (Year: 2008).*
(Continued)

*Primary Examiner* — Samuel C Woolwine
*Assistant Examiner* — Francesca Filippa Giammona
(74) *Attorney, Agent, or Firm* — MH2 Technology Law Group, LLP

(57) ABSTRACT

The present disclosure relates to a panel of ER regulated genes and method for using the panel for monitoring the response of an individual having cancer to treatment with amcenestrant, the method comprising determining a first ER activity score from a sample from the individual at a first time point before treatment with amcenestrant using the panel, then determining a second ER activity score from a sample from the individual at a second time point following administration of amcenestrant using the panel, and comparing the first ER activity score with the second ER activity score, wherein a decrease in the second ER activity score
(Continued)

relative to the first ER activity score is predictive of target engagement of amcenestrant.

14 Claims, 9 Drawing Sheets

(56) References Cited

FOREIGN PATENT DOCUMENTS

| | | | | |
|---|---|---|---|---|
| WO | WO-2015135035 A2 * | 9/2015 | ......... | C07K 16/2818 |
| WO | 2017140669 A1 | 8/2017 | | |
| WO | 2018091153 A1 | 5/2018 | | |
| WO | 2020037203 A2 | 2/2020 | | |

OTHER PUBLICATIONS

Wang et al., "Genome-Wide Investigation of Genes Regulated by ERa in Breast Cancer Cells," Molecules, vol. 23, pp. 1-20. (Year: 2018).*

Supplementary Table S1 for Wang et al. (Year: 2018).*

Besret et al., "Translational strategy using multiple nuclear imaging biomarkers to evaluate target engagement and early therapeutic efficacy of SAR439859, a novel selective estrogen receptor degrader", EJNMMI Research, vol. 10, pp. 1-13 (2020).

Chandarlapaty et al., "277MO SAR439859, an oral selective estrogen receptor (ER) degrader (SERD), in ER+/HER2− metastatic breast cancer (mBC): Biomarker analyses from a phase I/II study", Annals of Oncology, vol. 31, No. S4, (2020).

Heidari, Pedram et al., "Pharmacodynamic imaging guides dosing of a selective estrogen receptor degrader", Clin Cancer Res. vol. 21, No. 6, 1340-1347 (2015).

International Search Report and Written Opinion, International Application No. PCT/US2021/060349, Jun. 29, 2022, 24 pages.

Knudsen et al., "Development and Validation of a Gene Expression Score That Predicts Response to Fulvestrant in Breast Cancer Patients", PLOS ONE, vol. 9, No. 2 (2014).

Lee et al., "Development of a gene signature assessing ER modulation by SERMs and SERDs as a target engagement biomarker for endocrine therapy in breast cancer", Cancer Research, vol. 81, No. 13 Suppl (2021).

Lin et al., "Discovery of estrogen receptor [alpha] target genes and response elements in breast tumor cells", Genome Biology, vol. 5 (2004).

Nardone et al., "The oral selective oestrogen receptor degrader (SERD) AZD9496 is comparable to fulvestrant in antagonising ER and circumventing endocrine resistance", British Journal of Cancer, vol. 120, pp. 331-339 (2018).

Oza et al., "New Insights in Estrogen Receptor (ER) Biology and Implications for Treatment", Current Breast Cancer Reports, vol. 9, pp. 13-25 (2017).

Shomali et al., "Preclinical and clinical activity of SAR439859, Amcenestrant, a next generation SERD", Cancer Research, vol. 81, No. 13 Suppl (2021).

Shomali et al., "SAR439859, a Novel Selective Estrogen Receptor Degrader (SERD), Demonstrates Effective and Broad Antitumor Activity in Wild-Type and Mutant ER-Positive Breast Cancer Models", Molecular Cancer Therapeutics, vol. 20, pp. 250-262 (2020).

Sinn, Bruno V. et al., "SET ER/PR: a robust 18-gene predictor for sensitivity to endocrine therapy for metastatic breast cancer", npj Breast Cancer, vol. 5, No. 16; 8 pages (2019).

Symmans, W. Fraser et al., "Genomic Index of Sensitivity to Endocrine Therapy for Breast Cancer", Journal of Clinical Oncology, vol. 28, No. 27, pp. 4111-4119 (2010).

Welboren et al., "Identifying estrogen receptor target genes", Molecular Oncology, vol. 1, pp. 138-143 (2007).

* cited by examiner (300 nM)

AZD-SAR

(30 nM)

(300 nM)

GDC-SAR

(30 nM)

(300 nM)

SAR439859

(30 nM)

(300 nM)

Fulvestrant

(30 nM)

(300 nM)

GDC-0810

(30 nM)

(300 nM)

AZD9496

(30 nM)

-2 ▮▮▮▮▮▮▮ 2

Treatment (nM)

PANEL OF ER REGULATED GENES FOR USE IN MONITORING ENDOCRINE THERAPY IN BREAST CANCER

CROSS-REFERENCE TO RELATED APPLICATIONS

This application is a national phase entry pursuant to 35 U.S.C. § 371 of International Application No. PCT/US2021/060349, filed Nov. 22, 2021, which claims the benefit of priority to U.S. Provisional Application No. 63/117,229, filed Nov. 23, 2020, U.S. Provisional Application No. 63/173,107, filed Apr. 9, 2021, and European Application No. 21315066.7, filed Apr. 16, 2021, the contents of each of which are incorporated herein by reference in their entirety for all purposes.

BACKGROUND OF THE DISCLOSURE

The present disclosure describes panels of ER regulated genes which are useful for monitoring ER target engagement, including on-target activity, of endocrine therapy amcenestrant, as well as related kits. Shomali et al., SAR439859*, a Novel Selective Estrogen Receptor Degrader* (*SERD*), *Demonstrates Effective and Broad Antitumor Activity in Wild-Type and Mutant ER-Positive Breast Cancer Models*, Mol. Cancer Ther. (2021) is incorporated by reference herein in its entirety for all purposes.

Breast cancer is the most frequently diagnosed cancer in women. Estrogen receptor positive (ER+) cancer accounts for about 75% of all breast cancers.

Due to the dependency on ER signaling, the primary treatment approach for ER+ breast cancer has been to block estrogen function. Antihormonal therapies that directly antagonize the function of the estrogen receptor alpha (ERα; such as tamoxifen) or therapies that block the production of its ligand, estrogen (such as aromatase inhibitors), are the mainstay therapy for ER-positive (ER+) breast cancer. Although these treatments markedly reduce the risk of recurrence from early-stage disease and improve outcomes in patients with advanced disease, relapse frequently occurs after prolonged treatment. Recently, recurrent mutations have been identified in the ligand-binding domain of ERα in approximately 25-40% of patients who have relapsed after receiving one or more prior hormonal therapies. These mutations confer estrogen-independent, constitutive activity of the ERα, induction of tumor growth, reduced potency to anti-ERα therapies and complete resistance to aromatase inhibitors.

Some ligands that target the ERα can increase levels of the ERα protein steady state due to biological feedback mechanisms such as increases in the transcriptional compensation or thermodynamic stability upon ligand binding. For example, tamoxifen induces stabilization of the ERα protein, which adopts a conformation that may lead to agonist signaling. It has also been suggested that some mutations in the ERα, such as those affecting the Y537S or D538G amino acids, may be involved in stabilization of the ERα. Moreover, an increase in ERα stability could also result in ERα signaling leakage when continuous treatment coverage is not achieved. Altogether, there is rationale, in addition to ERα antagonism, that degradation of the ERα protein could have an impact on the ERα biology and efficacy of therapies targeting ERα.

Selective estrogen receptor modulators (SERMs) and selective estrogen receptor degraders (SERDs) have been developed to modulate ER activity.

Fulvestrant has been developed to overcome the partial modulation of ER transcriptional activity by SERMs. Selective estrogen receptor degraders (SERDs), such as fulvestrant, bind to the ERα to induce a conformational change that not only antagonizes ERα function, but also causes its proteasome-mediated degradation to more effectively inhibit ERα signaling. (Heidari et al. Pharmacodynamic Imaging Guides Dosing of a Selective Estrogen Receptor Degrader. Clin. *Cancer Res.* (2015)). Fulvestrant is an approved SERD indicated for the treatment of ER+ metastatic breast cancer in postmenopausal women with disease progression following anti-estrogen therapy. Fulvestrant has demonstrated preclinical and clinical benefits after failure of other hormonal therapies. However, fulvestrant, a steroid with a neutral and lipophilic side chain, requires unconventional long-acting intramuscular depot formulation, limiting its dose and exposure for maximal receptor engagement. The clinical benefit of fulvestrant is limited by its pharmaceutical properties, and burden of intramuscular administration.

To address the preceding pharmacological shortcomings posed by fulvestrant, several SERDs have entered clinical trials including GDC-0810 (NCT 01823835), AZD9496 (NCT02248090), AZD9833 (NCT03616586), GDC-0927 (NCT02316509) and GDC-9545 (NCT03916744, NCT03332797). These novel SERDs, which are chemically distinct from fulvestrant, can be classified into two major groups based on the chemical structure of their side chain that is key in driving ERα degradation. GDC-0927 is characterized by a fluoroalkylamine side chain, whereas GDC-0810, AZD9496 and LSZ102 each have a cinnamic acid side chain. It is not well understood whether the different side chains and/or their abilities to induce ERα degradation translate to differences in their biology and antitumor activities. Moreover, these SERDs have presented conflicting data in their relative abilities to induce ERα agonist activity or promote complete ERα degradation.

To better define the molecular features to achieve optimal clinical activity of SERDs, it is crucial to understand the relationship between the molecular structure of the drug, level of ERα degradation, and the subsequent impact on antitumor activity. Here, we describe amcenestrant (laboratory code SAR439859), a novel, non-steroidal, orally bioavailable SERD that bears a fluoropropyl pyrrolidinyl side chain and, unlike SERDs with a cinnamic acid side chain, SAR439859 has demonstrated strong ERα antagonist activity and potently induces its degradation, which results in improved efficacy of both in vitro and in vivo ER+ breast cancer models.

Currently, SERD activity in the clinic is measured by the degradation using IHC and on the inhibition of ER target gene progesterone receptor (PGR). Estrogens, which act as agonists, also promote degradation of the estrogen receptor therefore, degradation of ER alone is insufficient to determine the activity of SERDs on the ER pathway. While PGR is a well-established target gene of ER, ER is a transcription factor which regulates the transcription of many genes and PGR may not fully capture the activity of these molecules on the ER pathway.

Thus, a need exists for tools to monitor the response of individuals with cancer receiving treatment with SERDs, including amcenestrant, by predicting target engagement, including on-target activity. Because ER is a transcription factor that modulates the expression of a large set of genes, monitoring the expression level of a subset of those genes (i.e., gene signature) pretreatment and modulation of this gene signature posttreatment with amcenestrant may indicate target engagement, including on-target activity.

A gene signature provides information of the expression level of a specific group of genes in a cell or tissue. In breast cancer, gene signatures can complement classic prognostic factors (age, positive lymph nodes, tumor size, etc.) to give predictive and prognostic value. In breast cancer, for example, the 70-gene signature (MammaPrint) and the 21-gene signature (OncoType) are being used to identify patients who would most benefit from adjuvant therapy and is widely used in Europe and in the USA. Additional gene signatures have been developed to predict benefit from endocrine therapy in breast cancer, such as SET index, $SET_{ER/PR}$ for metastatic breast cancer (W. Symmans et al. in Journal of Clinical Oncology, Vol. 28, No. 27, 20 Sep. 2010, p. 4111-4119; B. Sinn et al. in Breast Cancer (2019)5:16), or the ER activity score published by Genentech/Hoffman-La Roche (WO 2020/037203).

ABBREVIATIONS

- DMSO dimethyl sulfoxide
- ER estrogen receptor
- ERα estrogen receptor alpha
- IHC immunohistochemistry
- IL interleukin
- LBD ligand-binding domain
- NA not applicable
- QD once daily
- Q2W every 2 weeks
- RT-qPCR reverse transcription-quantitative polymerase chain reach
- SERD selective ER degrader
- WT wild type

SUMMARY

Figure 1A:
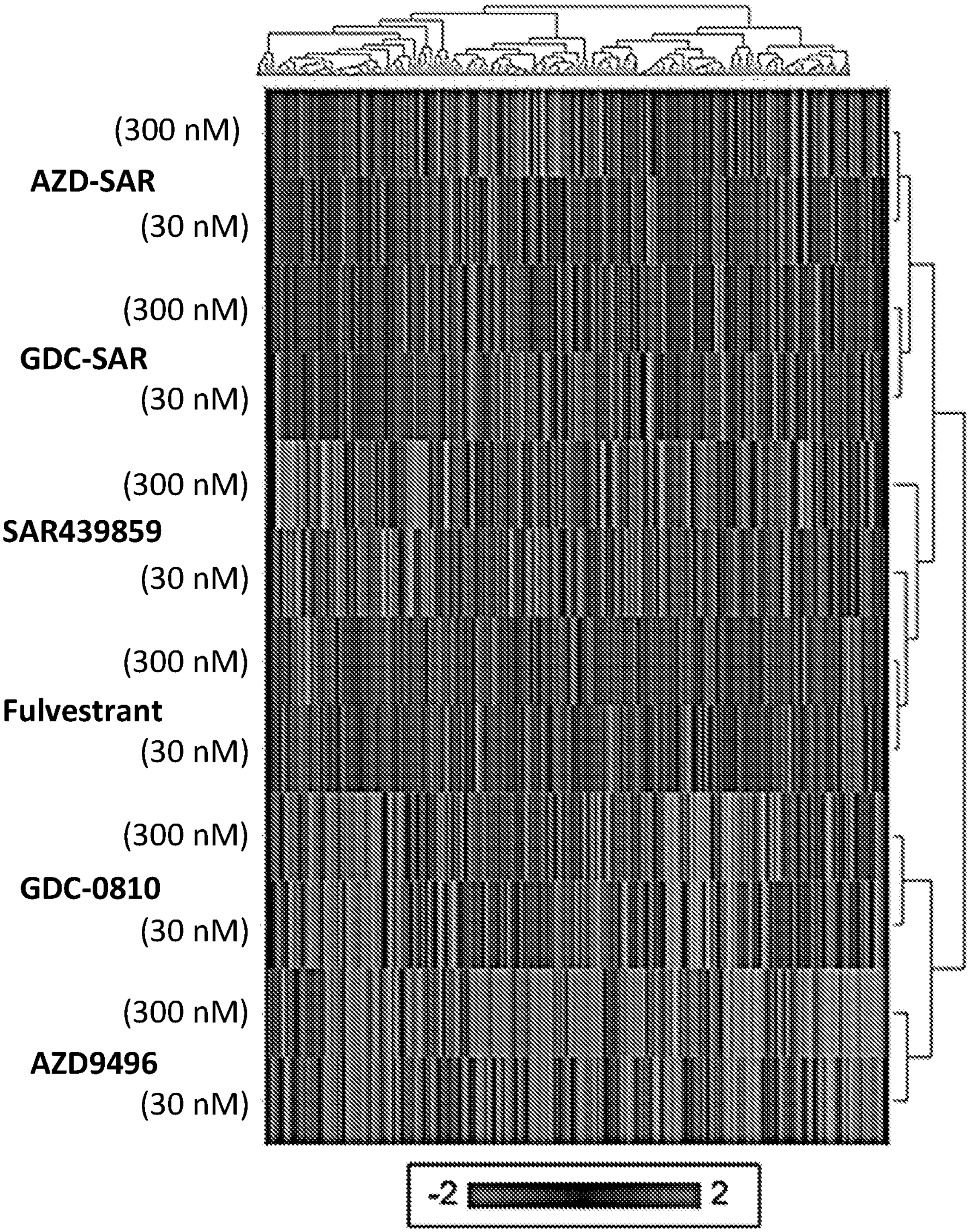
FIGS. 1A-D. A, Heat map of 1022 genes differentially expressed in the HCC1428 LTED breast cancer cell line in absence of exogenous estrogen at two doses (30 nM and 300 nM). Data was loge normalized followed by standardization and hierarchical clustering; B, Comparison of ER Scores with 6 SERDs/Assessment of the modulation of ER transcriptional activity by SERDs. ER transcriptional activity using ER signature and expressed as ER Activity Score from GSVA (Wilcoxon test is used to compare the means of delineated groups with  P<0.01 and * P<0.001) C, D reverse transcription-quantitative polymerase chain reach analysis of the effect of the different selective ER degrader molecules on the expression of ERα target genes CXCL12 and Bcas1. * Denotes significance (P<0.01) compared with unpaired t test.

Provided herein is a set of 87 genes with higher and lower expression levels, respectively identified from transcriptional profiling of cell lines to identify genes that are sensitive to estradiol, and ER antagonists, including SERDs. This set of ER regulated genes will be useful in monitoring the response of an individual having cancer to treatment with amcenestrant. The present disclosure includes, for example, any one or a combination of the following embodiments:

Embodiment 1. A panel of ER regulated genes having N genes, wherein N is at least 7 and equal to or less than about 87, and wherein the N genes comprise any 2 to 21 of the following upregulated genes: PTPRT, CAMK1D, BCAS1, ABCG1, KRT81, TLE2, SALL4, ITGB6, BBC3, IL1R1, CORO2A, GRM4, ATP6V0A4, MATN2, PPFIBP2, BMF, LOC283070, PSCA, BAK1, PLIN2, and SYNPO; and the N genes comprise any 5 to 66 of the following downregulated genes: H19, MYBL1, MGP, SLC5A8, PKIB, PGR, TMPRSS3, IGSF1, COL21A1, FSIP1, KLHL4, EGR3, NPY1R, HIST1H3C, GRIK3, SCNN1B, FRK, PRSS23, SERPINA5, SFXN2, CAP2, HIST1H2BM, CDC45, WDR62, DSCC1, GJA1, FAM196A, NTRK2, RAD54L, SDK2, SLC4A10, HIST1H4D, HIST1H4C, RGS22, SYBU, CA8, DIAPH3, FHL2, HIST1H1B, KCNH1, RAD51AP1, FANCD2, SLC39A8, SKP2, HIST1H3B, TMEM164, AURKB, DEPTOR, XRCC2, C1QTNF6, ERCC6L, ORC1, HIST2H2AC, RRM2, EME1, HIST1H2BF, CLSPN, EXO1, SDC2, HIST1H3I, HIST2H2AB, HIST1H4B, ASCL1, ATAD5, HIST1H1D, and HIST1H2BH.

Embodiment 2. The panel of embodiment 1, wherein N is 87, and wherein the 87 genes comprise the following 21 upregulated genes: PTPRT, CAMK1D, BCAS1, ABCG1, KRT81, TLE2, SALL4, ITGB6, BBC3, IL1R1, CORO2A, GRM4, ATP6V0A4, MATN2, PPFIBP2, BMF, LOC283070, PSCA, BAK1, PLIN2, and SYNPO; and the 87 genes comprise the following 66 downregulated genes: H19, MYBL1, MGP, SLC5A8, PKIB, PGR, TMPRSS3, IGSF1, COL21A1, FSIP1, KLHL4, EGR3, NPY1R, HIST1H3C, GRIK3, SCNN1B, FRK, PRSS23, SERPINA5, SFXN2, CAP2, HIST1H2BM, CDC45, WDR62, DSCC1, GJA1, FAM196A, NTRK2, RAD54L, SDK2, SLC4A10, HIST1H4D, HIST1H4C, RGS22, SYBU, CA8, DIAPH3, FHL2, HIST1H1B, KCNH1, RAD51AP1, FANCD2, SLC39A8, SKP2, HIST1H3B, TMEM164, AURKB, DEPTOR, XRCC2, C1QTNF6, ERCC6L, ORC1, HIST2H2AC, RRM2, EME1, HIST1H2BF, CLSPN, EXO1, SDC2, HIST1H3I, HIST2H2AB, HIST1H4B, ASCL1, ATAD5, HIST1H1D, and HIST1H2BH.

Embodiment 3. A method for monitoring the response of an individual having cancer to treatment with amcenestrant, the method comprising: (a) determining a first ER activity score from a sample from the individual at a first time point before treatment with amcenestrant; (b) following step (a), determining a second ER activity score from a sample from the individual at a second time point following administration of amcenestrant; and (c) comparing the first ER activity score with the second ER activity score, wherein a decrease in the second ER activity score relative to the first ER activity score is predictive of target engagement of amcenestrant, wherein determining the first ER activity score and the second ER activity score comprises analyzing a panel of ER regulated genes having N genes, wherein N is at least 7 and equal to or less than 87, and wherein the N genes comprise any 2 to 21 of the following upregulated genes: PTPRT, CAMK1D, BCAS1, ABCG1, KRT81, TLE2, SALL4, ITGB6, BBC3, IL1R1, CORO2A, GRM4, ATP6V0A4, MATN2, PPFIBP2, BMF, LOC283070, PSCA, BAK1, PLIN2, and SYNPO; and the N genes comprise any 5 to 66 of the following downregulated genes: H19, MYBL1, MGP, SLC5A8, PKIB, PGR, TMPRSS3, IGSF1, COL21A1, FSIP1, KLHL4, EGR3, NPY1R, HIST1H3C, GRIK3, SCNN1B, FRK, PRSS23, SERPINA5, SFXN2, CAP2, HIST1H2BM, CDC45, WDR62, DSCC1, GJA1, FAM196A, NTRK2, RAD54L, SDK2, SLC4A10, HIST1H4D, HIST1H4C, RGS22, SYBU, CA8, DIAPH3, FHL2, HIST1H1B, KCNH1, RAD51AP1, FANCD2, SLC39A8, SKP2, HIST1H3B, TMEM164, AURKB, DEPTOR, XRCC2, C1QTNF6, ERCC6L, ORC1, HIST2H2AC, RRM2, EME1, HIST1H2BF, CLSPN, EXO1, SDC2, HIST1H3I, HIST2H2AB, HIST1H4B, ASCL1, ATAD5, HIST1H1D, and HIST1H2BH.

Embodiment 4. The method of embodiment 3, wherein the panel of ER regulated genes has 87 genes, and wherein the 87 genes comprise the following 21 upregulated genes: PTPRT, CAMK1D, BCAS1, ABCG1, KRT81, TLE2, SALL4, ITGB6, BBC3, IL1R1, CORO2A, GRM4, ATP6V0A4, MATN2, PPFIBP2, BMF, LOC283070, PSCA, BAK1, PLIN2, and SYNPO; and wherein the 87 genes comprise the following 66 downregulated genes: H19, MYBL1, MGP, SLC5A8, PKIB, PGR, TMPRSS3, IGSF1, COL21A1, FSIP1, KLHL4, EGR3, NPY1R, HIST1H3C, GRIK3, SCNN1B, FRK, PRSS23, SERPINA5, SFXN2, CAP2, HIST1H2BM, CDC45, WDR62, DSCC1, GJA1, FAM196A, NTRK2, RAD54L, SDK2, SLC4A10, HIST1H4D, HIST1H4C, RGS22, SYBU, CA8, DIAPH3, FHL2, HIST1H1B, KCNH1, RAD51AP1, FANCD2, SLC39A8, SKP2, HIST1H3B, TMEM164, AURKB, DEPTOR, XRCC2, C1QTNF6, ERCC6L, ORC1, HIST2H2AC, RRM2, EME1, HIST1H2BF, CLSPN, EXO1, SDC2, HIST1H3I, HIST2H2AB, HIST1H4B, ASCL1, ATAD5, HIST1H1D, and HIST1H2BH.

Embodiment 5. The method of embodiments 3 or 4, wherein a decrease in the second ER activity score relative to the first ER activity score is predictive of on-target activity of amcenestrant.

Embodiment 6. The method of embodiment 5, wherein the on-target activity of amcenestrant comprises ER degradation and ER inhibition.

Embodiment 7. The method of any one of embodiments 3-6, wherein the method comprises contacting the sample from the individual with probes.

Embodiment 8. The method of any one of embodiments 3-7, wherein the method comprises detecting the RNA expression level of each of the N genes in the sample from the individual.

Embodiment 9. The method of any one of embodiments 3-8, wherein the method comprises RNA sequencing.

Embodiment 10. The method of any one of embodiments 3-9, wherein the individual has ER+ breast cancer.

Embodiment 11. The method of any one of embodiments 3-10, wherein the individual has HER2− breast cancer.

Embodiment 12. The method of any one of embodiments 3-11, wherein the individual has advanced or metastatic breast cancer.

Embodiment 13. The method of any one of embodiments 3-12, wherein the sample is a tumor biopsy.

Embodiment 14. The method of any one of embodiments 3-12, wherein the sample is a blood sample.

Embodiment 15. The method of any one of embodiments 3-12, wherein the sample is a serum sample.

Embodiment 16. The method of embodiment 13, wherein the tumor biopsy is a formalin-fixed tumor biopsy, a paraffin-embedded tumor biopsy, a formalin-fixed paraffin-embedded (FFPE) tumor biopsy, a fresh-frozen (FF) tumor biopsy, a frozen tumor biopsy, or a fresh tumor biopsy.

Embodiment 17. A kit comprising a set of probes for detecting expression of upregulated genes and downregulated genes;

wherein the upregulated genes comprise any 2 to 21 of PTPRT, CAMK1D, BCAS1, ABCG1, KRT81, TLE2, SALL4, ITGB6, BBC3, IL1R1, CORO2A, GRM4, ATP6V0A4, MATN2, PPFIBP2, BMF, LOC283070, PSCA, BAK1, PLIN2, and SYNPO; and wherein the downregulated genes comprise any 5 to 66 of H19, MYBL1, MGP, SLC5A8, PKIB, PGR, TMPRSS3, IGSF1, COL21A1, FSIP1, KLHL4, EGR3, NPY1R, HIST1H3C, GRIK3, SCNN1B, FRK, PRSS23, SERPINA5, SFXN2, CAP2, HIST1H2BM, CDC45, WDR62, DSCC1, GJA1, FAM196A, NTRK2, RAD54L, SDK2, SLC4A10, HIST1H4D, HIST1H4C, RGS22, SYBU, CA8, DIAPH3, FHL2, HIST1H1B, KCNH1, RAD51AP1, FANCD2, SLC39A8, SKP2, HIST1H3B, TMEM164, AURKB, DEPTOR, XRCC2, C1QTNF6, ERCC6L, ORC1, HIST2H2AC, RRM2, EME1, HIST1H2BF, CLSPN, EXO1, SDC2, HIST1H3I, HIST2H2AB, HIST1H4B, ASCL1, ATAD5, HIST1H1D, and HIST1H2BH.

Embodiment 18. The kit of embodiment 17, wherein the set of probes for detecting expression of upregulated genes and downregulated genes comprises probes to detect the upregulated genes PTPRT, CAMK1D, BCAS1, ABCG1, KRT81, TLE2, SALL4, ITGB6, BBC3, IL1R1, CORO2A, GRM4, ATP6V0A4, MATN2, PPFIBP2, BMF, LOC283070, PSCA, BAK1, PLIN2, and SYNPO; and comprises probes to detect the downregulated genes H19, MYBL1, MGP, SLC5A8, PKIB, PGR, TMPRSS3, IGSF1, COL21A1, FSIP1, KLHL4, EGR3, NPY1R, HIST1H3C, GRIK3, SCNN1B, FRK, PRSS23, SERPINA5, SFXN2, CAP2, HIST1H2BM, CDC45, WDR62, DSCC1, GJA1, FAM196A, NTRK2, RAD54L, SDK2, SLC4A10, HIST1H4D, HIST1H4C, RGS22, SYBU, CA8, DIAPH3, FHL2, HIST1H1B, KCNH1, RAD51AP1, FANCD2, SLC39A8, SKP2, HIST1H3B, TMEM164, AURKB, DEPTOR, XRCC2, C1QTNF6, ERCC6L, ORC1, HIST2H2AC, RRM2, EME1, HIST1H2BF, CLSPN, EXO1, SDC2, HIST1H3I, HIST2H2AB, HIST1H4B, ASCL1, ATAD5, HIST1H1D, and HIST1H2BH.

DETAILED DESCRIPTION

Definitions

The term “ER” or “estrogen receptor” refers to estrogen receptor a (gene name ESR1), a protein that binds to estradiol (E2). ER activates transcription of numerous genes and is a principal determinant of overall gene transcription in breast cancers. When bound to an estrogen, ERs may promote cell growth. An estrogen receptor positive (ER+) breast cancer typically indicates that the breast cancer cells depend upon estrogen for growth.

As used herein, a “panel” or “set” designates a group. For example, a “panel (or set) of ER regulated genes” as used herein, means a group of genes regulated by ER.

The term “upregulated genes” refers to genes that exhibit increased expression after administration of a single agent, such as amcenestrant, compared to treatment with a control, such as DMSO, or as compared to an earlier pre-treatment time point in the treated individual.

The term “downregulated genes” refers to genes that exhibit decreased expression after administration of a single agent, such as amcenestrant, compared to treatment with a control, such as DMSO, or as compared to an earlier pre-treatment time point in the treated individual.

The term “ER activity score,” as used herein, refers to a score obtained by using a computational method such as GSVA (Hanzelmann et al., GSVA: gene set variation analysis for microarray and RNA-seq data, in BMC Bioinformatics, 2013; 14:7, incorporated herein by reference in its entirety for its description of calculating scores using the GSVA method) on a gene expression data set obtained from a biological sample. An E2-induced score and an E2-suppressed score are calculated individually. An E2-induced score is calculated by using a computational method such as GSVA on a set of upregulated genes from a gene expression data set obtained from a biological sample. An E2-suppressed score is calculated by using a computational method such as GSVA on a set of downregulated genes from a gene expression data set obtained from a biological sample. The ER activity score is computed as follows: ER Activity Score=ER-induced score−E2-suppressed score.

“On-target activity of amcenestrant” refers to ER degradation and/or inhibition and can be shown, for example, by decrease of ER protein expression by immunohistochemistry, decrease of expression of proteins regulated by ER signaling pathway (Progesterone receptor, Ki67) by immunohistochemistry, and/or ER activity score by GSVA.

The term “advanced breast cancer” refers to a cancer wherein the tumor is not in a local regional area (i.e., it is outside of the primary tumor location), or if it cannot be removed by surgery.

The term “metastatic breast cancer” refers to a cancer which has spread to other sites of the body, such as the liver, lungs, bones, brain, and/or others.

ER Regulated Genes

In some embodiments, a panel of ER regulated genes is encompassed, wherein the panel of ER regulated genes has N genes, wherein N is at least 7 and equal to or less than about 87, and wherein the N genes comprise any 2 to 21 of the following upregulated genes: PTPRT, CAMK1D, BCAS1, ABCG1, KRT81, TLE2, SALL4, ITGB6, BBC3, IL1R1, CORO2A, GRM4, ATP6V0A4, MATN2, PPFIBP2, BMF, LOC283070, PSCA, BAK1, PLIN2, and SYNPO; and the N genes comprise any 5 to 66 of the following downregulated genes: H19, MYBL1, MGP, SLC5A8, PKIB, PGR, TMPRSS3, IGSF1, COL21A1, FSIP1, KLHL4, EGR3, NPY1R, HIST1H3C, GRIK3, SCNN1B, FRK, PRSS23, SERPINA5, SFXN2, CAP2, HIST1H2BM, CDC45, WDR62, DSCC1, GJA1, FAM196A, NTRK2, RAD54L, SDK2, SLC4A10, HIST1H4D, HIST1H4C, RGS22, SYBU, CA8, DIAPH3, FHL2, HIST1H1B, KCNH1, RAD51AP1, FANCD2, SLC39A8, SKP2, HIST1H3B, TMEM164, AURKB, DEPTOR, XRCC2, C1QTNF6, ERCC6L, ORC1, HIST2H2AC, RRM2, EME1, HIST1H2BF, CLSPN, EXO1, SDC2, HIST1H3I, HIST2H2AB, HIST1H4B, ASCL1, ATAD5, HIST1H1D, and HIST1H2BH.

In some embodiments, a panel of ER regulated genes is encompassed, wherein the panel of ER regulated genes has N genes, wherein N is equal to or less than about 87 and comprises at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, or 87 genes, and wherein the N genes comprise any 2 to 21, 3 to 21, 4 to 21, 5 to 21, 6 to 21, 7 to 21, 8 to 21, 9 to 21, 10 to 21, 11 to 21, 12 to 21, 13 to 21, 14 to 21, 15 to 21, 16 to 21, 17 to 21, 18 to 21, 19 to 21, 20 to 21, or 21 of the following upregulated genes: PTPRT, CAMK1D, BCAS1, ABCG1, KRT81, TLE2, SALL4, ITGB6, BBC3, IL1R1, CORO2A, GRM4, ATP6V0A4, MATN2, PPFIBP2, BMF, LOC283070, PSCA, BAK1, PLIN2, and SYNPO; and the N genes comprise any 5 to 66, 6 to 66, 7 to 66, 8 to 66, 9 to 66, 10 to 66, 11 to 66, 12 to 66, 13 to 66, 14 to 66, 15 to 66, 16 to 66, 17 to 66, 18 to 66, 19 to 66, 20 to 66, 21 to 66, 22 to 66, 23 to 66, 24 to 66, 25 to 66, 26 to 66, 27 to 66, 28 to 66, 29 to 66, 30 to 66, 31 to 66, 32 to 66, 33 to 66, 34 to 66, 35 to 66, 36 to 66, 37 to 66, 38 to 66, 39 to 66, 40 to 66, 41 to 66, 42 to 66, 43 to 66, 44 to 66, 45 to 66, 46 to 66, 47 to 66, 48 to 66, 49 to 66, 50 to 66, 51 to 66, 52 to 66, 53 to 66, 54 to 66, 55 to 66, 56 to 66, 57 to 66, 58 to 66, 59 to 66, 60 to 66, 61 to 66, 62 to 66, 63 to 66, 64 to 66, 65 to 66, or 66 of the following downregulated genes: H19, MYBL1, MGP, SLC5A8, PKIB, PGR, TMPRSS3, IGSF1, COL21A1, FSIP1, KLHL4, EGR3, NPY1R, HIST1H3C, GRIK3, SCNN1B, FRK, PRSS23, SERPINA5, SFXN2, CAP2, HIST1H2BM, CDC45, WDR62, DSCC1, GJA1, FAM196A, NTRK2, RAD54L, SDK2, SLC4A10, HIST1H4D, HIST1H4C, RGS22, SYBU, CA8, DIAPH3, FHL2, HIST1H1B, KCNH1, RAD51AP1, FANCD2, SLC39A8, SKP2, HIST1H3B, TMEM164, AURKB, DEPTOR, XRCC2, C1QTNF6, ERCC6L, ORC1, HIST2H2AC, RRM2, EME1, HIST1H2BF, CLSPN, EXO1, SDC2, HIST1H3I, HIST2H2AB, HIST1H4B, ASCL1, ATAD5, HIST1H1D, and HIST1H2BH.

In some embodiments, the panel of ER regulated genes has about 87 genes, including PTPRT, CAMK1D, BCAS1, ABCG1, KRT81, TLE2, SALL4, ITGB6, BBC3, IL1R1, CORO2A, GRM4, ATP6V0A4, MATN2, PPFIBP2, BMF, LOC283070, PSCA, BAK1, PLIN2, SYNPO, H19, MYBL1, MGP, SLC5A8, PKIB, PGR, TMPRSS3, IGSF1, COL21A1, FSIP1, KLHL4, EGR3, NPY1R, HIST1H3C, GRIK3, SCNN1B, FRK, PRSS23, SERPINA5, SFXN2, CAP2, HIST1H2BM, CDC45, WDR62, DSCC1, GJA1, FAM196A, NTRK2, RAD54L, SDK2, SLC4A10, HIST1H4D, HIST1H4C, RGS22, SYBU, CA8, DIAPH3, FHL2, HIST1H1B, KCNH1, RAD51AP1, FANCD2, SLC39A8, SKP2, HIST1H3B, TMEM164, AURKB, DEPTOR, XRCC2, C1QTNF6, ERCC6L, ORC1, HIST2H2AC, RRM2, EME1, HIST1H2BF, CLSPN, EXO1, SDC2, HIST1H3I, HIST2H2AB, HIST1H4B, ASCL1, ATAD5, HIST1H1D, and HIST1H2BH. Of the about 87 genes, 21 are upregulated genes: PTPRT, CAMK1D, BCAS1, ABCG1, KRT81, TLE2, SALL4, ITGB6, BBC3, IL1R1, CORO2A, GRM4, ATP6V0A4, MATN2, PPFIBP2, BMF, LOC283070, PSCA, BAK1, PLIN2, and SYNPO; and 66 are downregulated genes: H19, MYBL1, MGP, SLC5A8, PKIB, PGR, TMPRSS3, IGSF1, COL21A1, FSIP1, KLHL4, EGR3, NPY1R, HIST1H3C, GRIK3, SCNN1B, FRK, PRSS23, SERPINA5, SFXN2, CAP2, HIST1H2BM, CDC45, WDR62, DSCC1, GJA1, FAM196A, NTRK2, RAD54L, SDK2, SLC4A10, HIST1H4D, HIST1H4C, RGS22, SYBU, CA8, DIAPH3, FHL2, HIST1H1B, KCNH1, RAD51AP1, FANCD2, SLC39A8, SKP2, HIST1H3B, TMEM164, AURKB, DEPTOR, XRCC2, C1QTNF6, ERCC6L, ORC1, HIST2H2AC, RRM2, EME1, HIST1H2BF, CLSPN, EXO1, SDC2, HIST1H3I, HIST2H2AB, HIST1H4B, ASCL1, ATAD5, HIST1H1D, and HIST1H2BH.

Methods

In some embodiments, provided herein is a method for monitoring the response of an individual having cancer to treatment with amcenestrant, the method comprising: (a) determining a first ER activity score from a sample from the individual at a first time point before treatment with amcenestrant; (b) following step (a), determining a second ER activity score from a sample from the individual at a second time point following administration of amcenestrant; and (c) comparing the first ER activity score with the second ER activity score, wherein a decrease in the second ER activity score relative to the first ER activity score is predictive of target engagement of amcenestrant, wherein determining the first ER activity score and the second ER activity score comprises analyzing a panel of ER regulated genes having N genes, wherein N is at least 7 and equal to or less than about 87, and wherein the N genes comprise any 2 to 21 of the following upregulated genes: PTPRT, CAMK1D, BCAS1, ABCG1, KRT81, TLE2, SALL4, ITGB6, BBC3, IL1R1, CORO2A, GRM4, ATP6V0A4, MATN2, PPFIBP2, BMF, LOC283070, PSCA, BAK1, PLIN2, and SYNPO; and the N genes comprise any 5 to 66 of the following downregulated genes: H19, MYBL1, MGP, SLC5A8, PKIB, PGR, TMPRSS3, IGSF1, COL21A1, FSIP1, KLHL4, EGR3, NPY1R, HIST1H3C, GRIK3, SCNN1B, FRK, PRSS23, SERPINA5, SFXN2, CAP2, HIST1H2BM, CDC45, WDR62, DSCC1, GJA1, FAM196A, NTRK2, RAD54L, SDK2, SLC4A10, HIST1H4D, HIST1H4C, RGS22, SYBU, CA8, DIAPH3, FHL2, HIST1H1B, KCNH1, RAD51AP1, FANCD2, SLC39A8, SKP2, HIST1H3B, TMEM164, AURKB, DEPTOR, XRCC2, C1QTNF6, ERCC6L, ORC1, HIST2H2AC, RRM2, EME1, HIST1H2BF, CLSPN, EXO1, SDC2, HIST1H3I, HIST2H2AB, HIST1H4B, ASCL1, ATAD5, HIST1H1D, and HIST1H2BH.

In some embodiments, provided herein is a method for monitoring the response of an individual having cancer to treatment with amcenestrant, the method comprising: (a) determining a first ER activity score from a sample from the individual at a first time point before treatment with amcenestrant; (b) following step (a), determining a second ER activity score from a sample from the individual at a second time point following administration of amcenestrant; and (c) comparing the first ER activity score with the second ER activity score, wherein a decrease in the second ER activity score relative to the first ER activity score is predictive of target engagement of amcenestrant, wherein determining the first ER activity score and the second ER activity score comprises analyzing a panel of ER regulated genes having N genes, wherein N is equal to or less than about 87 and comprises at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, or 87 genes, and wherein the N genes comprise any 2 to 21, 3 to 21, 4 to 21, 5 to 21, 6 to 21, 7 to 21, 8 to 21, 9 to 21, to 21, 11 to 21, 12 to 21, 13 to 21, 14 to 21, 15 to 21, 16 to 21, 17 to 21, 18 to 21, 19 to 21, to 21, or 21 of the following upregulated genes: PTPRT, CAMK1D, BCAS1, ABCG1, KRT81, TLE2, SALL4, ITGB6, BBC3, IL1R1, CORO2A, GRM4, ATP6V0A4, MATN2, PPFIBP2, BMF, LOC283070, PSCA, BAK1, PLIN2, and SYNPO; and the N genes comprise any 5 to 66, 6 to 66, 7 to 66, 8 to 66, 9 to 66, 10 to 66, 11 to 66, 12 to 66, 13 to 66, 14 to 66, to 66, 16 to 66, 17 to 66, 18 to 66, 19 to 66, 20 to 66, 21 to 66, 22 to 66, 23 to 66, 24 to 66, to 66, 26 to 66, 27 to 66, 28 to 66, 29 to 66, 30 to 66, 31 to 66, 32 to 66, 33 to 66, 34 to 66, to 66, 36 to 66, 37 to 66, 38 to 66, 39 to 66, 40 to 66, 41 to 66, 42 to 66, 43 to 66, 44 to 66, to 66, 46 to 66, 47 to 66, 48 to 66, 49 to 66, 50 to 66, 51 to 66, 52 to 66, 53 to 66, 54 to 66, to 66, 56 to 66, 57 to 66, 58 to 66, 59 to 66, 60 to 66, 61 to 66, 62 to 66, 63 to 66, 64 to 66, to 66, or 66 of the following downregulated genes: H19, MYBL1, MGP, SLC5A8, PKIB, PGR, TMPRSS3, IGSF1, COL21A1, FSIP1, KLHL4, EGR3, NPY1R, HIST1H3C, GRIK3, SCNN1B, FRK, PRSS23, SERPINA5, SFXN2, CAP2, HIST1H2BM, CDC45, WDR62, DSCC1, GJA1, FAM196A, NTRK2, RAD54L, SDK2, SLC4A10, HIST1H4D, HIST1H4C, RGS22, SYBU, CA8, DIAPH3, FHL2, HIST1H1B, KCNH1, RAD51AP1, FANCD2, SLC39A8, SKP2, HIST1H3B, TMEM164, AURKB, DEPTOR, XRCC2, C1QTNF6, ERCC6L, ORC1, HIST2H2AC, RRM2, EME1, HIST1H2BF, CLSPN, EXO1, SDC2, HIST1H3I, HIST2H2AB, HIST1H4B, ASCL1, ATAD5, HIST1H1D, and HIST1H2BH.

In some embodiments, provided herein is a method for monitoring the response of an individual having cancer to treatment with amcenestrant, the method comprising: (a) determining a first ER activity score from a sample from the individual at a first time point before treatment with amcenestrant; (b) following step (a), determining a second ER activity score from a sample from the individual at a second time point following administration of amcenestrant; and (c) comparing the first ER activity score with the second ER activity score, wherein a decrease in the second ER activity score relative to the first ER activity score is predictive of target engagement of amcenestrant, wherein determining the first ER activity score and the second ER activity score comprises analyzing a panel of ER regulated genes having about 87 genes, wherein the 21 genes are upregulated genes: PTPRT, CAMK1D, BCAS1, ABCG1, KRT81, TLE2, SALL4, ITGB6, BBC3, IL1R1, CORO2A, GRM4, ATP6V0A4, MATN2, PPFIBP2, BMF, LOC283070, PSCA, BAK1, PLIN2, and SYNPO; and wherein 66 genes are downregulated genes: H19, MYBL1, MGP, SLC5A8, PKIB, PGR, TMPRSS3, IGSF1, COL21A1, FSIP1, KLHL4, EGR3, NPY1R, HIST1H3C, GRIK3, SCNN1B, FRK, PRSS23, SERPINA5, SFXN2, CAP2, HIST1H2BM, CDC45, WDR62, DSCC1, GJA1, FAM196A, NTRK2, RAD54L, SDK2, SLC4A10, HIST1H4D, HIST1H4C, RGS22, SYBU, CA8, DIAPH3, FHL2, HIST1H1B, KCNH1, RAD51AP1, FANCD2, SLC39A8, SKP2, HIST1H3B, TMEM164, AURKB, DEPTOR, XRCC2, C1QTNF6, ERCC6L, ORC1, HIST2H2AC, RRM2, EME1, HIST1H2BF, CLSPN, EXO1, SDC2, HIST1H3I, HIST2H2AB, HIST1H4B, ASCL1, ATAD5, HIST1H1D, and HIST1H2BH.

In some embodiments, a decrease in the second ER activity score relative to the first ER activity score is predictive of on-target activity of amcenestrant. In some embodiments, the on-target activity of amcenestrant comprises ER degradation and ER inhibition.

Assay/RNA Sequencing

In some embodiments, the expression level of a gene may be a nucleic acid expression level, such as an RNA expression level, an mRNA expression level, or a DNA expression level. Any suitable method of determining a nucleic acid expression level may be used. In some embodiments, the nucleic acid expression level is determined using RNA-seq. For example, the nucleic acid expression level could be determined using an RNA ACCESS protocol or TRUSEQ RIBO-ZERO00 protocol (ILLUMINA)), RT-qPCR, qPCR, multiplex qPCR or RT-qPCR, microarray analysis, SAGE, MassARRAY techniques, or a combination thereof.

Methods for the evaluation of mRNAs in cells are well known and include, for example, RNA sequencing (RNA-seq), whole genome sequencing (WGS), serial analysis of gene expression (SAGE), and various nucleic acid amplification assays such as RT-PCR, using complementary primers specific for the predetermined set of genes. In some embodiments, qRT-PCR is used. In addition, such methods can include one or more steps that allow one to determine the levels of target mRNA in a biological sample, for example, by simultaneously examining the levels of a comparative control mRNA sequence of a "housekeeping" gene such as an actin family member. In some embodiments, the sequence of the amplified target cDNA can be determined. Optional methods include protocols which examine or detect mRNAs, such as target mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes whose expression correlates with target engagement, including on-target activity, of treatment comprising amcenestrant may be arrayed on a solid support. For example, any of the 87 genes of Table 3 may be arrayed on a solid support. Hybridization of a labeled probe with a particular array member indicates that the sample from which the probe was derived expresses that gene.

Biological Samples

Any biological sample comprising one or more tumor cell(s) can be used in the methods disclosed herein. In some embodiments, the sample is selected from a tumor biopsy, a blood sample, a serum sample, or any combination thereof. In some embodiments, the sample is a tumor biopsy. In some embodiments, the sample obtained from the subject is a formalin-fixed tumor biopsy. In some embodiments, the sample obtained from the subject is a formalin-fixed paraffin-embedded tumor (FFPE) biopsy or a paraffin-embedded tumor biopsy. In some embodiments, the sample obtained from the subject is a fresh-frozen (FF) tumor biopsy. In some embodiments, the sample is a fresh tumor biopsy. In some embodiments, the sample is an archival tumor biopsy. In some embodiments, the sample is a frozen tumor biopsy.

In some instances of any of the methods and assays, the sample is obtained from the individual prior to administration of amcenestrant as described herein. In some embodiments, the sample is obtained minutes, hours, days, weeks, months, or years prior to administration of amcenestrant as described herein. In other words, the sample may be a baseline sample. In some embodiments, the sample is obtained from the individual following administration of amcenestrant as described herein. In some instances, the sample from the individual is obtained within thirty hours following administration of an endocrine therapy. In some embodiments, the sample is obtained minutes, hours, or days following administration of amcenestrant as described herein. In some embodiments, multiple samples are obtained from the same individual at different time points, for example, prior to and following administration of amcenestrant as described herein.

SERD Compound

In some embodiments, the SERD compound is SAR439859 (amcenestrant). Synthesis of SAR439859 is described in patent application WO2017140669 (Example 51). SAR439859 (amcenestrant) is 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid. SAR439859 (amcenestrant) has the following chemical formula:

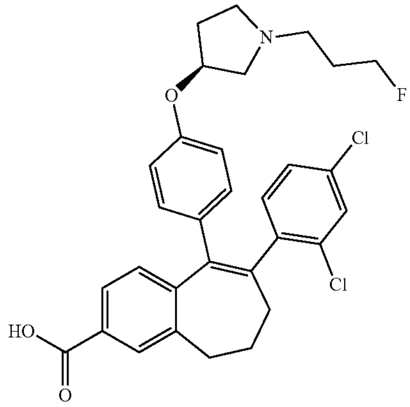 [SMILES: O=C(O)c1ccc2c(c1)CCCC(c1ccc(Cl)cc1Cl)=C2c1ccc(O[C@H]2CCN(CCCF)C2)cc1]

Additional Anticancer Therapies

In some embodiments, the methods disclosed herein further comprise administering amcenestrant and an additional anticancer therapy. The additional anticancer therapy can comprise any therapy known in the art for the treatment of a tumor in a subject and/or any standard-of-care therapy. In some embodiments, the additional anticancer therapy comprises a surgery, a radiation therapy, a chemotherapy, an immunotherapy, a hormone therapy, or any combination thereof. In some embodiments, the additional anticancer therapy comprises a chemotherapy. In some embodiments, the additional anticancer therapy comprises an immunotherapy. In some embodiments, the additional anticancer therapy comprises a hormone therapy.

In some embodiments, the anticancer therapy is palbociclib. In some embodiments, the anticancer therapy is alpelisib.

Cancers

In some embodiments, the disclosure is directed to a method of monitoring the response of an individual having cancer to treatment with amcenestrant.

In some embodiments, the cancer is breast cancer, preferably ER+/HER2− advanced or metastatic breast cancer.

Kits and Articles of Manufacture

In some embodiments, provided herein is a kit or an article of manufacture containing materials useful for monitoring the response of an individual having cancer to treatment with amcenestrant. In some embodiments, the kit or article of manufacture comprises a first set of probes for detecting expression of upregulated genes and downregulated genes; wherein the upregulated genes comprise any 2 to 21, 3 to 21, 4 to 21, 5 to 21, 6 to 21, 7 to 21, 8 to 21, 9 to 21, 10 to 21, 11 to 21, 12 to 21, 13 to 21, 14 to 21, 15 to 21, 16 to 21, 17 to 21, 18 to 21, 19 to 21, 20 to 21, or 21 of PTPRT, CAMK1D, BCAS1, ABCG1, KRT81, TLE2, SALL4, ITGB6, BBC3, IL1R1, CORO2A, GRM4, ATP6V0A4, MATN2, PPFIBP2, BMF, LOC283070, PSCA, BAK1, PLIN2, and SYNPO; and wherein the downregulated genes comprise any 5 to 66, 6 to 66, 7 to 66, 8 to 66, 9 to 66, 10 to 66, 11 to 66, 12 to 66, 13 to 66, 14 to 66, 15 to 66, 16 to 66, 17 to 66, 18 to 66, 19 to 66, 20 to 66, 21 to 66, 22 to 66, 23 to 66, 24 to 66, 25 to 66, 26 to 66, 27 to 66, 28 to 66, 29 to 66, 30 to 66, 31 to 66, 32 to 66, 33 to 66, 34 to 66, 35 to 66, 36 to 66, 37 to 66, 38 to 66, 39 to 66, 40 to 66, 41 to 66, 42 to 66, 43 to 66, 44 to 66, 45 to 66, 46 to 66, 47 to 66, 48 to 66, 49 to 66, 50 to 66, 51 to 66, 52 to 66, 53 to 66, 54 to 66, 55 to 66, 56 to 66, 57 to 66, 58 to 66, 59 to 66, 60 to 66, 61 to 66, 62 to 66, 63 to 66, 64 to 66, 65 to 66, or 66 of H19, MYBL1, MGP, SLC5A8, PKIB, PGR, TMPRSS3, IGSF1, COL21A1, FSIP1, KLHL4, EGR3, NPY1R, HIST1H3C, GRIK3, SCNN1B, FRK, PRSS23, SERPINA5, SFXN2, CAP2, HIST1H2BM, CDC45, WDR62, DSCC1, GJA1, FAM196A, NTRK2, RAD54L, SDK2, SLC4A10, HIST1H4D, HIST1H4C, RGS22, SYBU, CA8, DIAPH3, FHL2, HIST1H1B, KCNH1, RAD51AP1, FANCD2, SLC39A8, SKP2, HIST1H3B, TMEM164, AURKB, DEPTOR, XRCC2, C1QTNF6, ERCC6L, ORC1, HIST2H2AC, RRM2, EME1, HIST1H2BF, CLSPN, EXO1, SDC2, HIST1H3I, HIST2H2AB, HIST1H4B, ASCL1, ATAD5, HIST1H1D, and HIST1H2BH.

In some embodiments, the kit or article of manufacture comprises a first set of probes for detecting expression of upregulated genes and downregulated genes; wherein the upregulated genes comprise PTPRT, CAMK1D, BCAS1, ABCG1, KRT81, TLE2, SALL4, ITGB6, BBC3, IL1R1, CORO2A, GRM4, ATP6V0A4, MATN2, PPFIBP2, BMF, LOC283070, PSCA, BAK1, PLIN2, and SYNPO; and wherein the downregulated genes comprise H19, MYBL1, MGP, SLC5A8, PKIB, PGR, TMPRSS3, IGSF1, COL21A1, FSIP1, KLHL4, EGR3, NPY1R, HIST1H3C, GRIK3, SCNN1B, FRK, PRSS23, SERPINA5, SFXN2, CAP2, HIST1H2BM, CDC45, WDR62, DSCC1, GJA1, FAM196A, NTRK2, RAD54L, SDK2, SLC4A10, HIST1H4D, HIST1H4C, RGS22, SYBU, CA8, DIAPH3, FHL2, HIST1H1B, KCNH1, RAD51AP1, FANCD2, SLC39A8, SKP2, HIST1H3B, TMEM164, AURKB, DEPTOR, XRCC2, C1QTNF6, ERCC6L, ORC1, HIST2H2AC, RRM2, EME1, HIST1H2BF, CLSPN, EXO1, SDC2, HIST1H3I, HIST2H2AB, HIST1H4B, ASCL1, ATAD5, HIST1H1D, and HIST1H2BH.

In some embodiments, the kit or article of manufacture may include one or more reagents for preparing a sample for RNA sequencing analysis. In some embodiments, the sample is selected from a tumor biopsy, a blood sample, a serum sample, or any combination thereof. In some embodiments, the sample is a tumor biopsy. In some embodiments, the sample obtained from the subject is a formalin-fixed tumor biopsy. In some embodiments, the sample obtained from the subject is a formalin-fixed paraffin-embedded tumor (FFPE) biopsy or a paraffin-embedded tumor biopsy. In some embodiments, the sample obtained from the subject is a fresh-frozen (FF) tumor biopsy. In some embodiments, the sample is a fresh tumor biopsy. In some embodiments, the sample is an archival tumor biopsy. In some embodiments, the sample is a frozen tumor biopsy.

In some embodiments, the kit or article of manufacture further includes one or more reagents for determining an ER activity score from a sample.

In some embodiments, the kit or article of manufacture may include instructions to use the kit to monitor and/or assess the response of an individual having a breast cancer to treatment with amcenestrant, as described herein.

In some embodiments, the kit or article of manufacture may include a container, a label on the container, and a composition contained within the container, wherein the composition includes one or more polynucleotides that hybridize to a complement of a gene listed herein (for example, any genes in Table 3) under stringent conditions, and the label on the container indicates that the composition can be used to evaluate the activity of a set of genes listed herein in Table 3 in a sample, and wherein the kit includes instructions for using the polynucleotide(s) for evaluating the presence of the genes' RNA or DNA in a particular sample type.

In some embodiments, the kit or article of manufacture is oligonucleotide-based and may include, for example (1) an oligonucleotide, for example a detectably labeled oligonucleotide, which hybridizes to a nucleic acid sequence encoding a protein or (2) a pair of primers useful for amplifying a nucleic acid molecule. In some embodiments, the kit or article of manufacture may also include a buffering agent, a preservative, or a protein stabilizing agent. In some embodiments, the kit or article of manufacture may further include components necessary for detecting the detectable label, for example, an enzyme or a substrate. In some embodiments, the kit or article of manufacture may also contain a control sample or a series of control samples that can be assayed and compared to the test sample. In some embodiments, each component of the kit or article of manufacture can be enclosed within an individual container and all of the various containers can be within a single package, along with instructions for interpreting the results of the assays performed using the kit or article of manufacture.

Example 1

Materials and Methods

Key details of the materials and methods used are provided below.

Cell Culture and Reagents

MCF7, CAMA-1, ZR-75-1, MDAMB134VI, MDAMB361, BT474, BT473, MDAMB415, EFM19, HCC1428, HCC1500, HEK293T, MDAMB231 and SUM44PE cells were purchased from ATCC or Asterand and underwent authentication using short tandem repeat (STR) DNA profiling at Idexx. The HCC1428 LTED cell line was obtained from Carlos Arteaga (TW Miller et al. in Clinical Cancer Research, 2011; 17:2024-2034). All cell lines were routinely screened for mycoplasma contamination using Lonza Mycoalert and Stratagene Mycosensor. Unless otherwise indicated, tissue culture supplements and medium were purchased from Hyclone, Corning or Invitrogen. Cells were maintained as recommended by ATCC. HCC1428-LTED was maintained in phenol red-free improved modified eagle's medium (IMEM, Corning) with 10% dextran-charcoal-treated (CSS) FBS (Hyclone). SUM44PE was maintained as previously described in IMEM with 2% CSS. HCI-013 was established from a pleural effusion in a 53-year-old woman with metastatic ER+/progesterone receptor-positive/human epidermal growth factor receptor 2-negative invasive lobular carcinoma (gifted from Alana Welms). Fulvestrant, 40H-tamoxifen, raloxifene, bazedoxifene and 170-estradiol were purchased from Sigma Aldrich.

Compounds

SAR439859 was synthesized as described in patent application WO2017140669 (example 51). GDC0810 and AZD9496 were synthesized as described in WO2012037410 (Example 111) and WO2014191726 (Example 1), respectively. Both AZD-SAR and GDC-SAR were made as described in WO2018091153 (Example 255 and 256, respectively).

RNA Isolation and Quantitative Polymerase Chain (qPCR)

RNA was extracted using the RNeasy kit (Qiagen) per the manufacturers instruction, quantified by NanoDrop 8000 (ThermoScientific) and reverse-transcribed with cDNA archive kit (Applied Biosystems). Taqman gene expression assays (Applied Biosystems) were used to quantify PGR (Hs00172183_m1), Bcas 1 (Hs00952822_m1), CXCL12 (Hs03676656_mH), BLNK1(Hs00929914_m1), IL20 (Hs00218888_m1) and the house-keeping genes PGK (Hs00391480_m1) and GAPDH (Hs99999905 ml) The relative quantities were determined using ΔΔ threshold cycle (ΔΔCt), according to the manufacturer's instructions (Applied Biosystems).

RNA Sequencing/Development of Panel of ER Regulated Genes

To develop a panel of ER regulated genes, an experiment was performed as follows. First, MCF-7 cells were treated with DMSO, estradiol (E2), 2 SERM and 5 SERD compounds individually at three concentrations. See Table 1 below, which shows the treatment scheme for treatment of MCF-7 cells with a single agent (DMSO, estradiol, SERMs, or SERDs). The concentration unit is nM.

TABLE 1

| Treatment | Type | Low | Mid | High |
|---|---|---|---|---|
| DMSO | Control | | | |
| Estradiol | Agonist | 0.3 | 1 | 3 |
| Bazodoxifene | SERM | 2 | 6 | 20 |
| Tamoxifen | SERM | 6 | 20 | 60 |
| Fulvestrant | SERD | 2 | 6 | 20 |
| RA03504902 | SERD | 2 | 6 | 20 |
| RA08425393 | SERD | 5 | 15 | 50 |
| GDC-0810 | SERD | 5 | 15 | 50 |
| RU58688 | SERD | 2 | 6 | 20 |

Second, MCF-7 cells were treated with a combination of estradiol and one of the SERD and SERD compounds. See Table 2 below, which shows the treatment scheme for treatment for MCF-7 cells with estradiol plus one of 2 SERMs and 5 SERDs. The concentration unit is nM.

TABLE 2

| Treatment | Type | SERD/SERM Conc |
|---|---|---|
| Estradiol + Bazodoxifene | Agonist + SERM | 20 (nM) |
| Estradiol + Tamoxifen | Agonist + SERM | 60 (nM) |
| Estradiol + Fulvestrant | Agonist + SERD | 20 (nM) |
| Estradiol + RA03504902 | Agonist + SERD | 20 (nM) |
| Estradiol + RA08425393 | Agonist + SERD | 50 (nM) |
| Estradiol + GDC-0810 | Agonist + SERD | 50 (nM) |
| Estradiol + RU58688 | Agonist + SERD | 20 (nM) |

RNA was extracted using the RNeasy kit (Qiagen) according to the manufacturer's protocol. The concentration of RNA samples was determined using NanoDrop 8000 (ThermoScientific) and the integrity of RNA was determined by 4200 TapeStation (Agilent Technologies).

An RNA-seq library of 96 SERD RNA samples was prepared using a kit from NuGen Ovation® Universal RNA-Seq System Method (Illumina® Platforms) conforming to the manufacturer's protocol. The 50 bp rapid single-read flow cell was used to sequence the library on the Illumina HiSeq 2500 in the rapid mode. RNA-seq data were processed as follows: RNA sequencing FASTQ files were mapped to the reference genome GRCh 38 using Spliced Transcripts Alignment to a Reference (STAR) aligner (Dobin et al. in Bioinformatics, January 2013, Vol. 29, Issue 1, p. 15-21) and Cufflinks to generate gene-level estimation of expression in transcripts per million (TPM). TPM was calculated as calculated measured as an expression unit and then quantile-normalized and log 2-transformed. RNA-seq data generated from this cell line analysis identified genes that were significantly up- and down-regulated by E2 relative to DMSO. ER-regulated genes were identified using two comparisons. First, genes were identified that were modulated by one or more SERM or SERD compounds in Table 1 and modulated in the opposite direction by estradiol ([log 2 FC]>2 and FDR<0.05 vs. DMSO control). To identify genes that are differentially expressed between SERD compound treatment and dimethyl sulfoxide (DMSO; control) treatment groups, a two-factor (treatment and dose) analysis of variance (ANOVA) model was used at respective dose and time points. The treatment factor was fixed, with seven levels: six SERD compounds and the DMSO control. The dose factor was also fixed, with two levels: low and high. All samples were treated at 24h. Post hoc contrast analyses were performed at each dose and time level, between each SERD compound treatment and the DMSO control. Cut-off levels of absolute fold-change≥1.5 and false discovery rate-adjusted p-value≤0.05 were used to select differentially expressed genes (DEGs), which resulted in a panel of 1022 DEGs. This analysis was performed using Array Studio (Qiagen). The panel of 1022 genes identified as differentially expressed in at least one compound-versus-DMSO comparison were used for hierarchical clustering of compound treatment data normalized to DMSO control at respective dose and time points. Complete-linkage clustering was performed based on Pearson correlation coefficients. Expression profile similarity between compounds was assessed by Pearson correlation on the differentially expressed genes.

Figure 5:
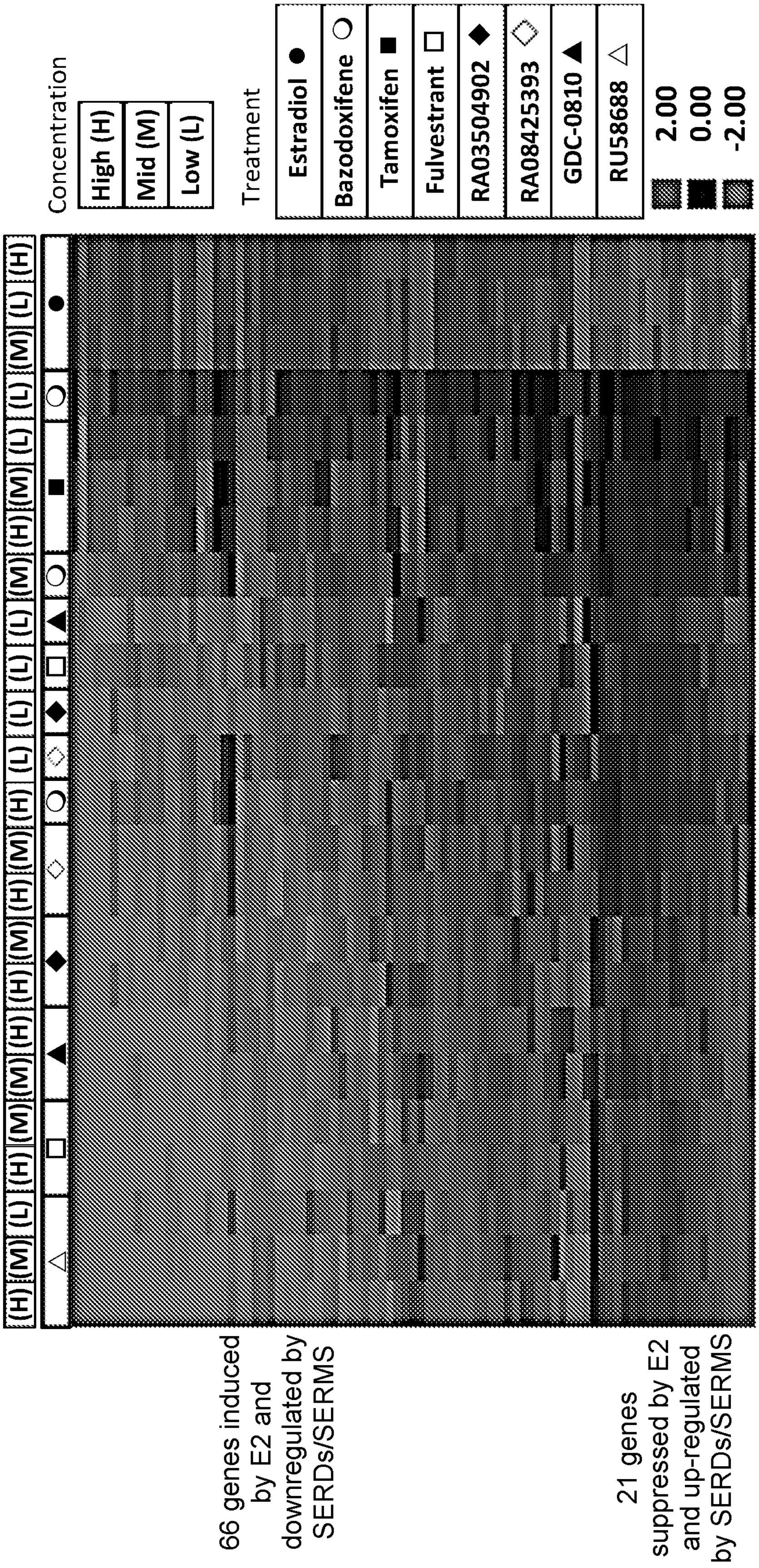
FIG. 5. ER activity signature. Heatmap shows the DMSO-normalized gene expression of 87 genes in ER activity signature. Sixty-six genes are induced by E2 and downregulated by SERDs/SERMs and twenty-one genes suppressed by E2 and upregulated by SERDs/SERMs.

Second, genes were identified that were modulated by one or more SERM or SERD molecules in the presence of estradiol ([log 2 FC]>2 and FDR<0.05 vs. estradiol alone) (see Table 2). 87 genes were modulated in both comparisons. Among the 87 genes, there are 66 genes induced by E2 and downregulated by SERDs/SERMs and 21 genes suppressed by E2 and upregulated by SERDs/SERMs. This signature can be used to measure ER modulation by SERMs and SERDs. In general, the 87 genes were modulated more strongly by SERD compounds than by SERM compounds; see FIG. 5.

Results

Figure 3:
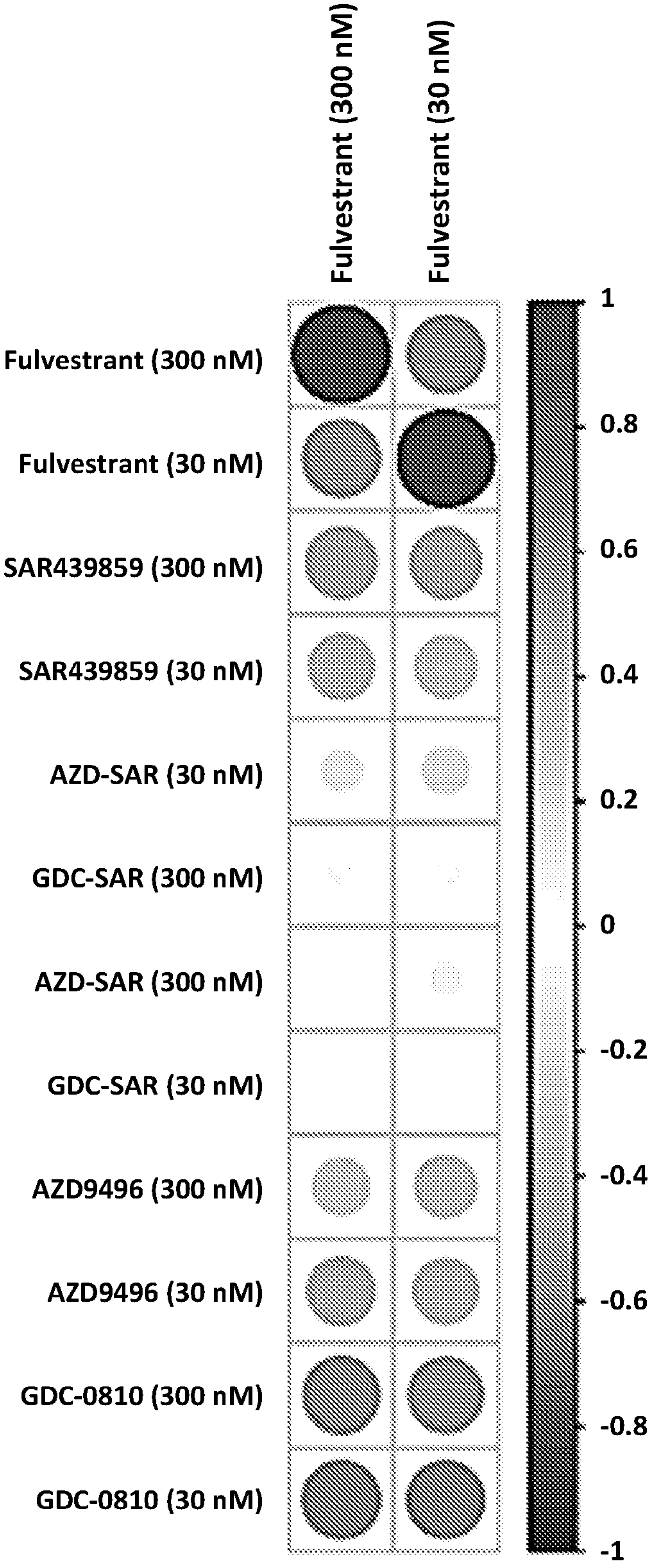
FIG. 3. Correlation of gene expression profile similarity between SERDs in HCI013 PDX tumor model. The panel of 1022 genes identified as differentially expressed in at least one compound-versus-DMSO comparison were used for hierarchical clustering of compound treatment data normalized to DMSO control at respective dose and time points. Expression profile similarity between compounds was assessed by Pearson correlation on the differentially expressed genes.

To evaluate the ER modulation by amcenestrant and other SERDs, we treated HCC1428-LTED (long term estrogen deprived) breast cancer cell lines with SERD compounds at either 300 nM (high) or 30 nM (low) in 24 hours. To unmask the ER-intrinsic activity, we then evaluated gene expression after compound treatment in HCC1428-LTED cells, which is a cell line that is hormone-deprived. Changes in global mRNA expression were assessed 24 hours post treatment. Hierarchical clustering on a selected panel of 1022 transcripts identified two groups with differing signatures: one group included GDC-0810 and AZD9496, and the other group included fulvestrant, SAR439859, GDC-SAR and AZD-SAR (FIG. 1A). Our ER activity score analysis showed that two SERDs, fulvestrant and SAR439859, strongly reduced the ER activity score as did two hybrid molecules, GDC-SAR and AZD-SAR. In contrast, GDC-0810 and AZD9496 only partially reduced the ER activity score. Statistical correlation revealed that the SAR439859-induced expression profile is closely correlated to fulvestrant. On the other hand, GDC-0810 and AZD9496 transcript profiles only weakly correlated to that of fulvestrant. Interestingly, the profiles of the hybrid molecules GDC-SAR and AZD-SAR, are also closely correlated to those of fulvestrant and SAR439859 (FIG. 1A; FIG. 3).

In general, the 87 genes were modulated more strongly by SERD compounds than by SERM compounds. Among the 87 genes, there are 66 genes induced by E2 and down-regulated by SERDs/SERMs and 21 genes suppressed by E2 and up-regulated by SERDs/SERMs.

To assess the relative ER modulating activity of the compounds, a panel of ER regulated genes (87 genes, Table 3) was developed by transcriptional profiling of multiple cell lines to identify genes that were modulated by estradiol and then blocked by SERM and SERD. This panel of ER regulated genes can be used to measure ER modulation by SERMs and SERDs. An ER Activity Score was then assessed using gene set variation analysis (GSVA) on the ER Signature (BMC Bioinformatics. 2013; 14:7).

Figure 1B:
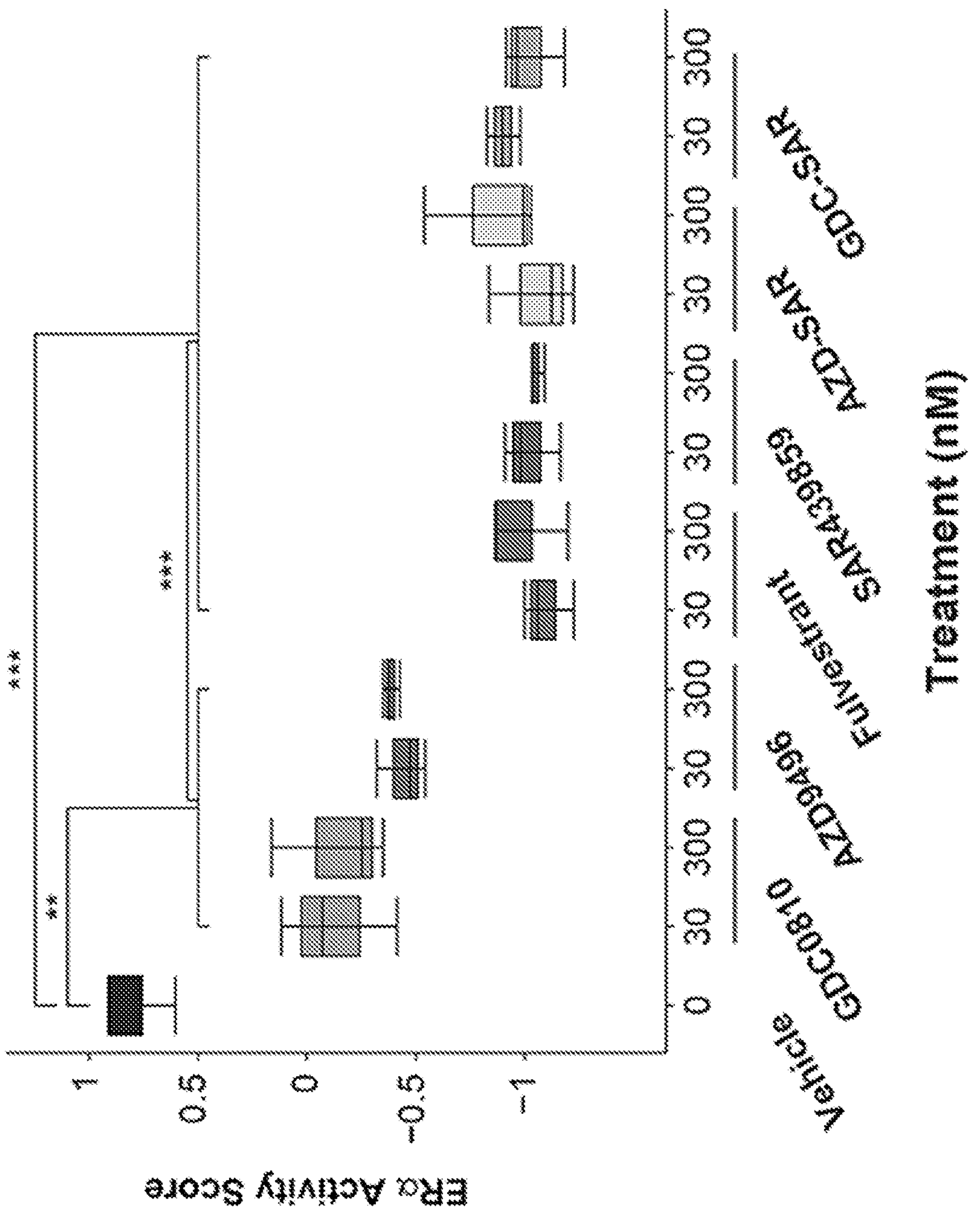
Figure 1D:
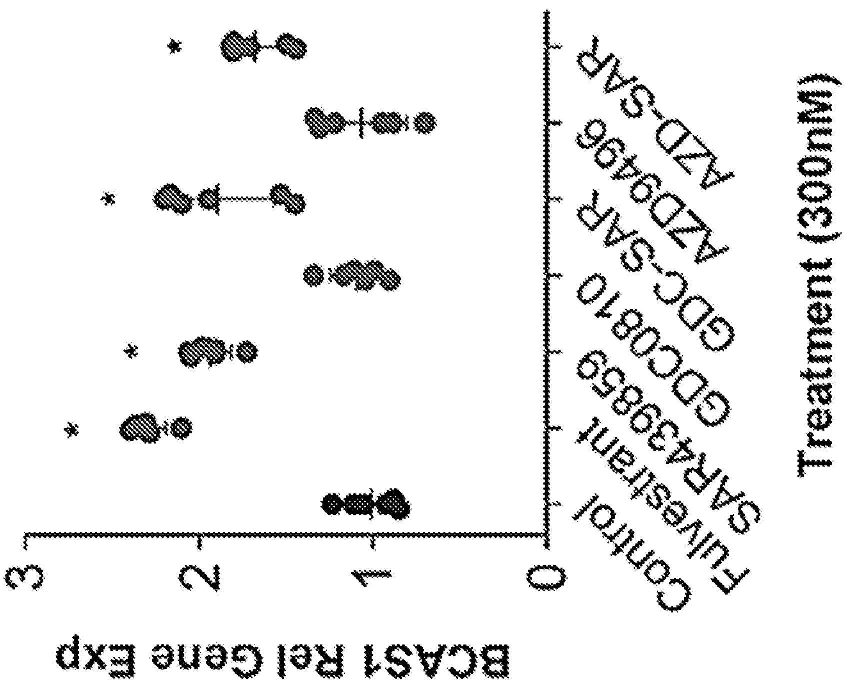
Figure 1C:
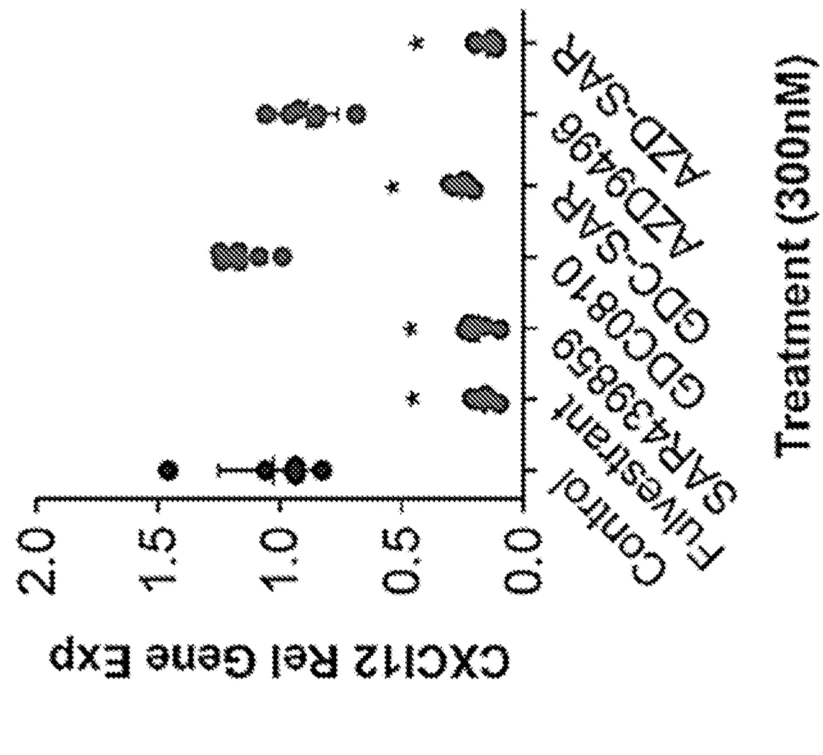

Fulvestrant and SAR439859 demonstrated a deep inhibition of ER activity, while GDC-0810 and AZD9496 only partially inhibited ERα activity further supporting the above observations. Interestingly, both hybrid molecules, GDC-SAR and AZD-SAR, also strongly inhibited ERα transcriptional activity (FIG. 1B). Findings were confirmed by measuring the expression of two well-validated ER target genes, CXCL12 and BCAS1, by RT-qPCR. Gene expression analysis provided further confirmation of the differential response of these molecules on well-validated ERα target genes (Elife. 2016; 5, Endocr Relat Cancer. 2015; 22(5):713-24). SAR439859, GDC-SAR, and AZD-SAR inhibited expression of CXCL12 and induced expression of Bcas 1, whereas GDC-0810 and AZD9496 failed to elicit any significant change in the expression of these genes (FIG. 1C, D). Remarkably, SAR439859 and fulvestrant induced a profound modulation of ERα intrinsic activity in the absence of E2, suggesting a strong inverse agonist activity of these compounds.

The list provided below are genes that are either down-regulated or up-regulated by treatment with SERDs and more specifically, amcenestrant.

TABLE 3

List of genes

| Symbol | Class |
|---|---|
| H19 | SERD_down |
| MYBL1 | SERD_down |
| MGP | SERD_down |
| SLC5A8 | SERD_down |
| PKIB | SERD_down |
| PGR | SERD_down |
| TMPRSS3 | SERD_down |
| IGSF1 | SERD_down |
| COL21A1 | SERD_down |
| FSIP1 | SERD_down |
| KLHL4 | SERD_down |
| EGR3 | SERD_down |
| NPY1R | SERD_down |
| HIST1H3C | SERD_down |
| GRIK3 | SERD_down |
| SCNN1B | SERD_down |
| FRK | SERD_down |
| PRSS23 | SERD_down |
| SERPINA5 | SERD_down |
| SFXN2 | SERD_down |
| CAP2 | SERD_down |
| HIST1H2BM | SERD_down |
| CDC45 | SERD_down |
| WDR62 | SERD_down |
| DSCC1 | SERD_down |
| GJA1 | SERD_down |
| FAM196A | SERD_down |
| NTRK2 | SERD_down |
| RAD54L | SERD_down |
| SDK2 | SERD_down |
| SLC4A10 | SERD_down |
| HIST1H4D | SERD_down |

TABLE 3-continued

| List of genes | |
|---|---|
| Symbol | Class |
| HIST1H4C | SERD_down |
| RGS22 | SERD_down |
| SYBU | SERD_down |
| CA8 | SERD_down |
| DIAPH3 | SERD_down |
| FHL2 | SERD_down |
| HIST1H1B | SERD_down |
| KCNH1 | SERD_down |
| RAD51AP1 | SERD_down |
| FANCD2 | SERD_down |
| SLC39A8 | SERD_down |
| SKP2 | SERD_down |
| HIST1H3B | SERD_down |
| TMEM164 | SERD_down |
| AURKB | SERD_down |
| DEPTOR | SERD_down |
| XRCC2 | SERD_down |
| C1QTNF6 | SERD_down |
| ERCC6L | SERD_down |
| ORC1 | SERD_down |
| HIST2H2AC | SERD_down |
| RRM2 | SERD_down |
| EME1 | SERD_down |
| HIST1H2BF | SERD_down |
| CLSPN | SERD_down |
| EXO1 | SERD_down |
| SDC2 | SERD_down |
| HIST1H3I | SERD_down |
| HIST2H2AB | SERD_down |
| HIST1H4B | SERD_down |
| ASCL1 | SERD_down |
| ATAD5 | SERD_down |
| HIST1H1D | SERD_down |
| HIST1H2BH | SERD_down |
| PTPRT | SERD_up |
| CAMK1D | SERD_up |
| BCAS1 | SERD_up |
| ABCG1 | SERD_up |
| KRT81 | SERD_up |
| TLE2 | SERD_up |
| SALL4 | SERD_up |
| ITGB6 | SERD_up |
| BBC3 | SERD_up |
| IL1R1 | SERD_up |
| CORO2A | SERD_up |
| GRM4 | SERD_up |
| ATP6V0A4 | SERD_up |
| MATN2 | SERD_up |
| PPFIBP2 | SERD_up |
| BMF | SERD_up |
| LOC283070 | SERD_up |
| PSCA | SERD_up |
| BAK1 | SERD_up |
| PLIN2 | SERD_up |
| SYNPO | SERD_up |

Figure 2:
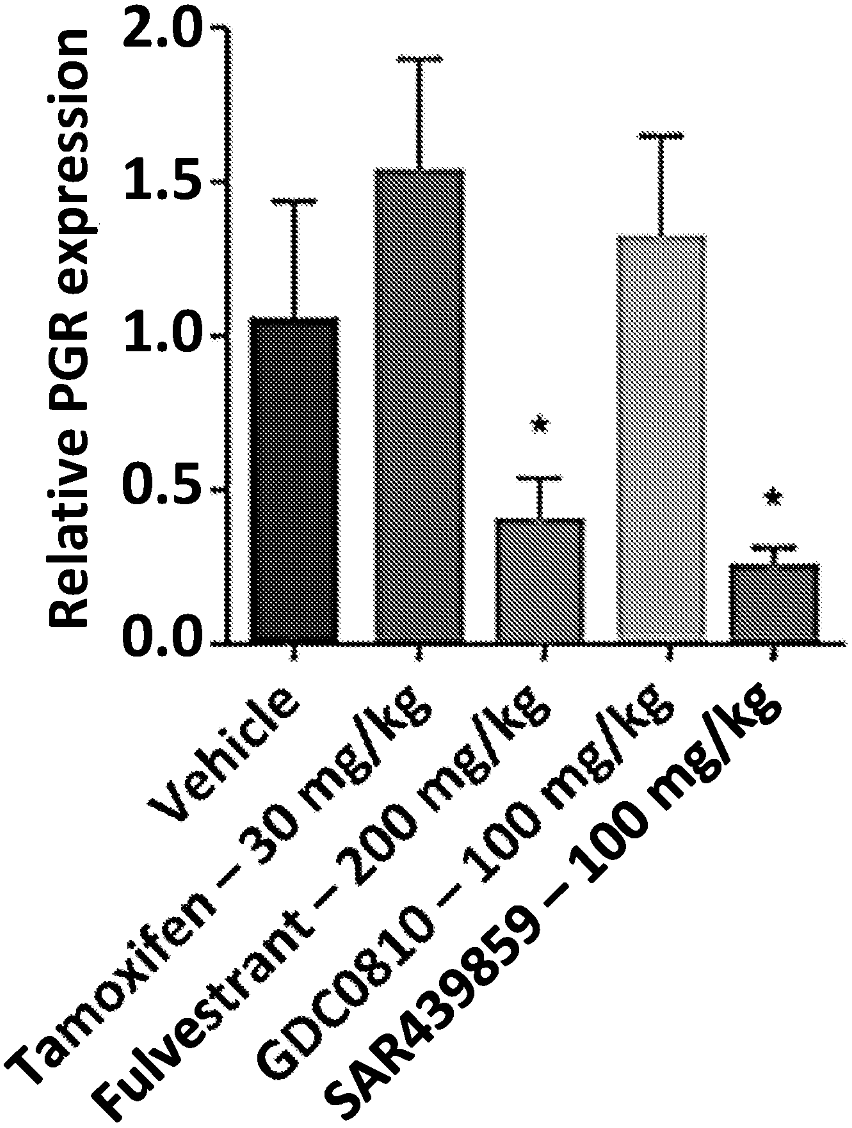
FIG. 2. Analysis of PGR gene expression in tumors collected 8 hours after the last administration of tamoxifen (30 mg/kg), fulvestrant (200 mg/kg), GDC0810 (100 mg/kg), and SAR439859 (100 mg/kg). For FIG. 2 *P<0.05; denotes significance compared to vehicle treated group at end of study using unpaired t test.
Figure 4A:
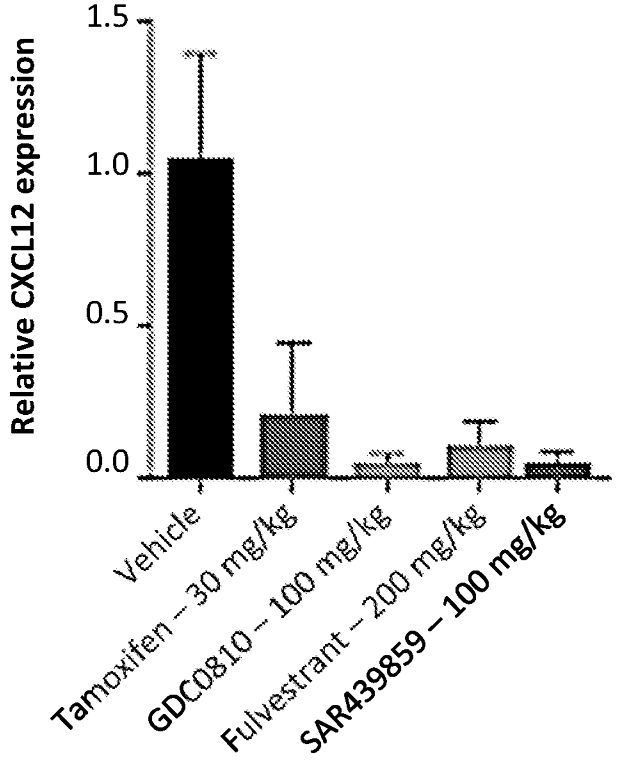
FIGS. 4A-B. Evaluation of target gene modulation in ERα ligands in an endocrine therapy-resistant tumor model. Gene expression analysis of (A) CXCL12 and (B) ER activity score in HCI013 PDX tumor model 8 h after the last administration of tamoxifen (30 mg/kg, QD), GDC0810 (100 mg/kg, QD), fulvestrant (200 mg/kg, Q2W) and SAR439859 (100 mg/kg, QD). Data represent mean and standard deviation for 3 replicates for CXCL12 gene expression. An ER Signature of 87 genes was that were modulated by estradiol and then blocked by SERM and SERD compounds was used to calculate the ER Activity Score and was assessed using gene set variation analysis (GSVA). Data represents the mean and deviation from the mean for each of the described treatments.
Figure 4B:
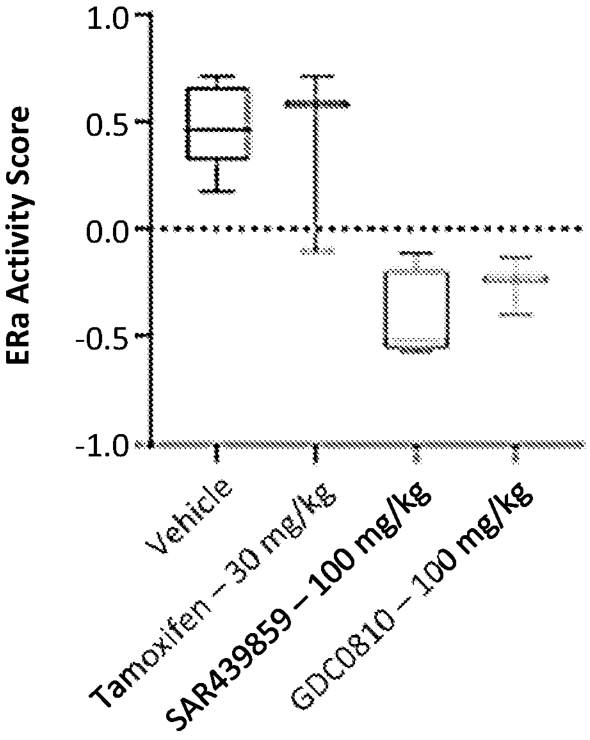

RT-qPCR analysis of individual ERα repressed genes such as PGR and CXCL12 confirmed stronger inhibition by SAR439859 compared to fulvestrant or GDC-0810 in HCI013 tumors (FIG. 2 and FIG. 4A, respectively). The ERα transcriptional activity was analyzed in the HCI013 model using the panel of genes corresponding to the ER gene signature derived from the in vitro cell line analysis as previously described. Both SAR439859 and GDC-0810 treatments displayed suppressive activity of ERα signaling, with more marked ERα suppression achieved by SAR439859 compared with GDC-0810 (FIG. 4B).

Example 2

The study was an open-label, Phase 1/2 study among postmenopausal women with ER+/HER2− advanced/metastatic breast cancer that evaluated the safety, antitumor activity, pharmacokinetics, and pharmacodynamics of amcenestrant administered as monotherapy in dose escalation (Part A) and dose expansion (Part B) cohorts, and in combination therapies in other arms of the study. There was a screening period comprising 28 days before baseline to baseline. The treatment period included 28-day cycles of therapy wherein SAR439859 was administered. After the end of treatment, there was a follow-up period. In Part A, dose escalation, 20-600 mg PO (oral) QD (once daily) of SAR439859 was administered. In Part B, dose expansion, 400 mg PO QD of SAR439859 was administered.

Paired tumor biopsies were collected at screening and at the end of Cycle 2 (Cycle 2, Day 28) in patients from Part B who provided consent for their collection. For each biopsy, formalin-fixed paraffin-embedded (FFPE) tissue (blocks or slides) were collected of 5 μm each for immunohistochemistry (IHC) analysis, and of 10 μm each for RNA extraction and subsequent RNA-seq analysis. IHC ER, progesterone receptor (PgR), and Ki67 protein expression slides were assessed by two expert pathologists (VP and A-LB). IHC staining was performed on the Ventana Discovery XT IHC platform using anti-ER clone SP1 (CONFIRM Anti-Estrogen Receptor, Roche, ref 790-4325), anti-PgR clone 1E2 (CONFIRM Anti-progesterone receptor, Roche, ref 790-4296), and anti-Ki67 clone 30-9 (CONFIRM Anti-Ki-67, Roche, Ref 790-4286). Stained slides were evaluated by standard light microscopy using a manual scoring system. Staining was evaluated in tumor cells only. For ER and PgR expression, H-scores were calculated. For Ki67 protein expression, the percentage of positive tumor cells was calculated. Total RNA was extracted from FFPE tissue (slides of 10 μm). A targeted-enrichment RNA-seq approach was applied utilizing KAPA RNA HyperPrep and whole exome SeqCap kits (Roche) followed by the generation of sequencing reads with NextSeq 500 (Illumina). RNA-seq FASTQ files were processed with STAR aligner and Cufflinks to generate gene-level fragments per kilobase of transcript per million mapped reads (FPKM). Those FPKM values were converted to gene-level estimation of expression in transcripts per million (TPM). The TPM data were then quantile-normalized and log 2-transformed. RNA-seq analysis determined decreases in the ER activation score measured by gene set variation analysis (GSVA) as previously described.

Plasma samples were collected at Cycle 1, Day 1 and at the end of Cycle 2, Day 28 to assess ESR1 mutations.

Wild-type and mutant ESR1 status in circulating free DNA (cfDNA) was determined. cfDNA was measured at baseline and at 56 days in the treatment period. cfDNA was evaluated for hot-spot, pathogenic ESR1 mutations (single nucleotide variants) in the ligand binding domain of ESR1 by multiplex central droplet digital polymerase chain reaction (dd-PCR) BEAMing 12-gene assay using the OncoBEAM™ platform by Sysmex Inostics (Baltimore, MD, USA). cfDNA was also measured in a different way at baseline and at the end of treatment, using Roche AVENIO expanded panel, 77-gene NGS panel (Ambry Genetics). At baseline, germline mutations were assessed. Saliva mutation calls as reference for possible germline mutations in cfDNA.

Amcenestrant induced ER degradation/signaling inhibition as evidenced in paired tumor biopsies (collected at baseline and after two 28-days cycles of amcenestrant administration). In one patient, on-treatment biopsy was collected at day fifteen of first cycle of administration.

Figure 6A:
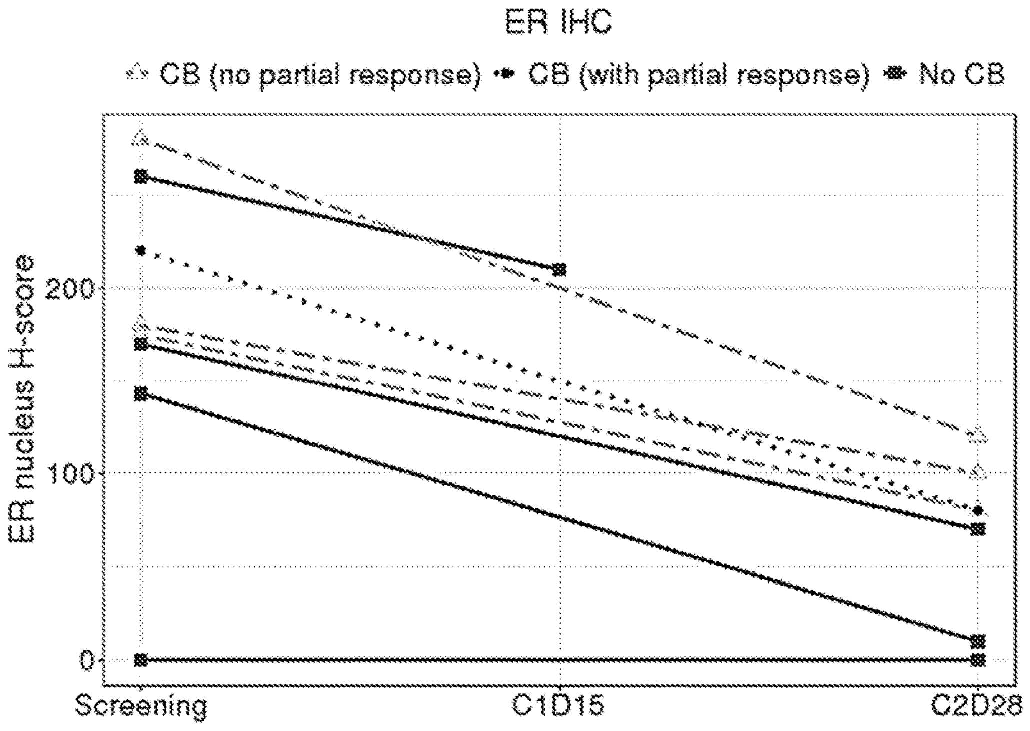
FIGS. 6A-D. On-target estrogen receptor degradation/pathway inhibition during amcenestrant therapy as shown by changes from screening to Cycle 2, Day 28 (i.e., pre- and post-treatment) in A, ER nucleus H-score by IHC (IHC ER expression); B, PgR nucleus H-score by IHC; and C, percent of positive cells showing Ki67 protein expression by IHC; D, pre-post ER activation scores by GSVA (ER activity score based on RNA-seq data from paired tumor biopsies). *Each line in each of FIGS. 6A-D indicates a single patient with available data at baseline/screening and post-baseline. There are 8 patients represented in FIG. 6A. There are 8 patients represented in FIG. 6B; some of the lines in FIG. 6B overlap. There are 8 patients represented in FIG. 6C. There are 5 patients represented in FIG. 6D. C1D1, Cycle 1, Day 1; C2D28, Cycle 2, Day 28; CB, clinical benefit (complete response+partial response+stable disease≥24 weeks); ER, estrogen receptor; ESR1, estrogen receptor 1; GSVA, gene set variation analysis; IHC, immunohistochemistry; PgR, progesterone receptor.
Figure 6B:
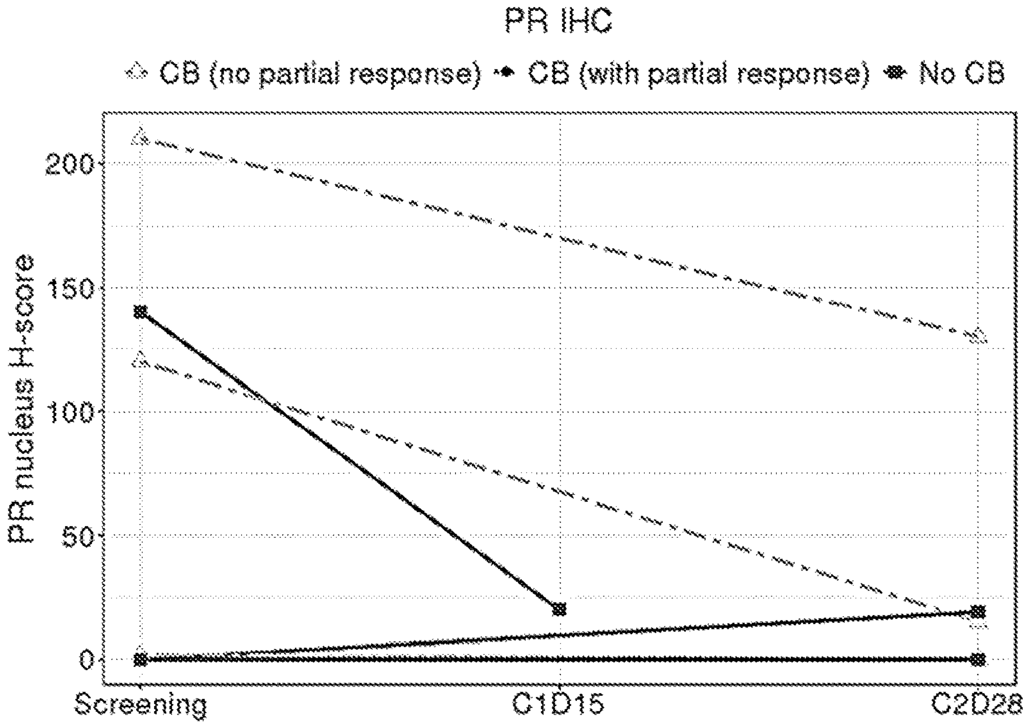
Figure 6C:
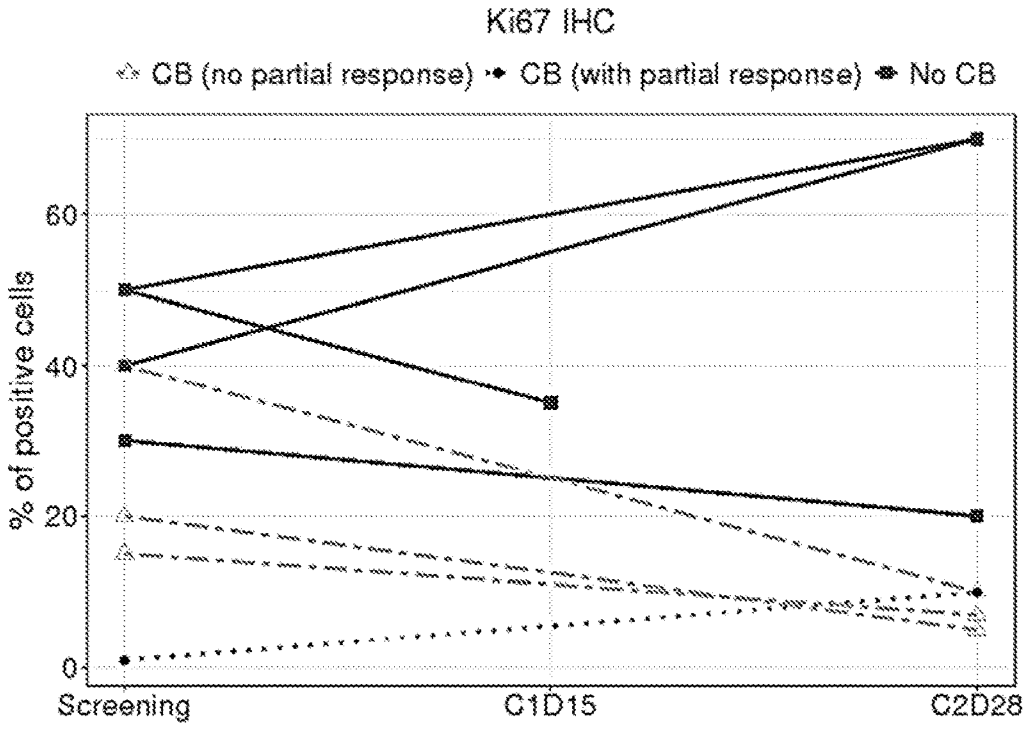
Figure 6D:
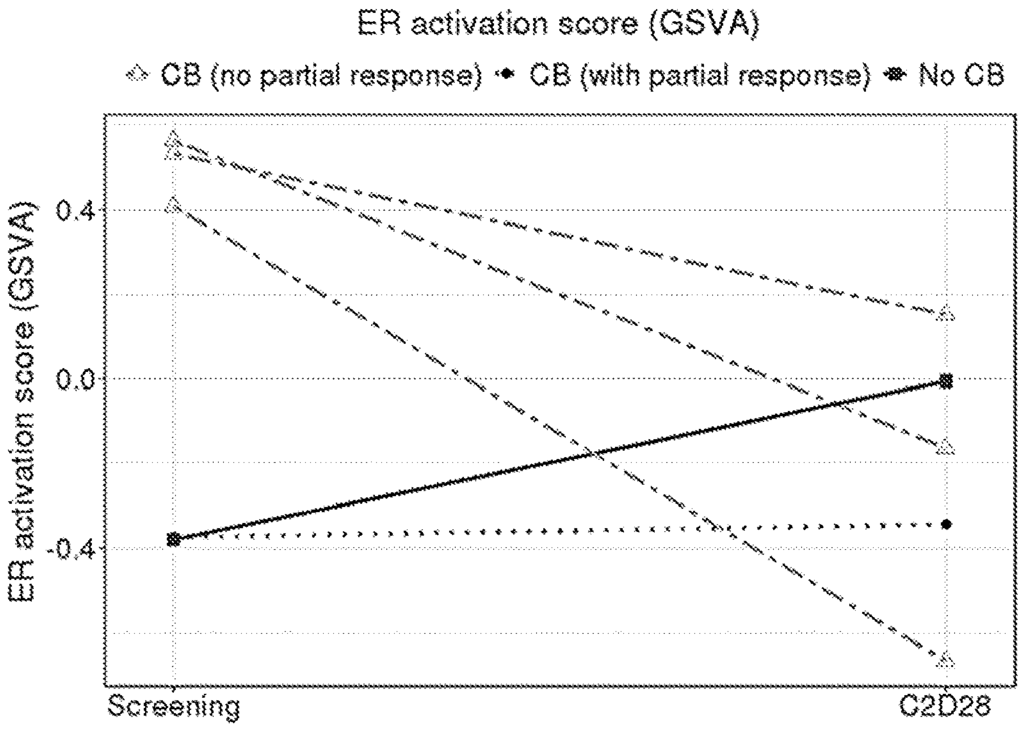

Amcenestrant demonstrated robust on-target activity as shown by overall reductions in IHC ER expression (ER degradation) (FIG. 6A; median relative change from baseline was −58% [range−93% to −44%] among patients with non-zero values at screening and available data at Cycle 2, Day 28; n=6), reduction in PgR expression (FIG. 6B; median relative change from screening was −88% [range−100% to −38%]; n=3), reduction in Ki67 protein expression (FIG. 6C; median change from screening in percentage of Ki67 positive cells was −8% [range −30% to +30%]; n=7), and reduction in ER activation score by GSVA (FIG. 6D; median change from screening was −0.4 [range −1.1 to +0.4]; n=5). ER or PgR nucleus H-scores decreased at Cycle 2, Day 28 in all patients with non-zero screening values. Among patients with ER or PgR nucleus H-scores equal to zero at screening, one patient had an increase in PgR nucleus H-score at Cycle 2, Day 28. ER activation score decreased or remained stable only among patients who showed clinical benefit (median change from screening was −0.6 [range −1.1 to 0]; n=4), while ER activation score increased for the patient with no clinical benefit (change from screening: +0.4). The "(n=)" numbers above indicate the number of patients for whom descriptive statistics (either median change or median relative change) were calculated. The numbers of patients with available data at baseline/screening and post-baseline (each line in each of FIGS. 6A-D representing a single patient) can be different from the "(n=)" numbers above, at least because median relative change was not calculated when baseline/screening was equal to zero.

Response for purposes of clinical benefit assessment was assessed per RECIST v1.1.

ER activity score (evaluated in 5-paired biopsies) decreased or remained stable among patients who showed clinical benefit, while for the patient with no clinical benefit it increased. In patients who showed clinical benefit without partial response, ER activity score decreased. In one patient that achieved both clinical benefit and partial response, there was no change in activation score (hence the baseline score was very low, indicative of low ER activity).

The ER activity score correlated more closely with clinical benefit (CB) than ER protein IHC did. Among all methods used to assess on-target activity of amcenestrant in tumor biopsies (immunohistochemistry and transcriptome analysis), ER activity score had the most clear distinction among patients that achieve clinical benefit or not. Levels of IHC ER protein did not always correlate with ER pathway status.

The application of the ER activity score to preclinical and clinical studies illustrates potential value as biomarkers such as target engagement pharmacodynamic (PD) biomarker for SERDs.

Study strengths include the combined evaluation of safety, antitumor activity and pharmacokinetics/pharmacodynamics demonstrating robust target engagement and ER degradation/pathway inhibition in ER+/HER2− advanced breast cancer.

What is claimed is:

1. A method for monitoring the response of an individual having cancer to treatment with amcenestrant, the method comprising: (a) determining a first ER activity score from a first sample from the individual at a first time point before treatment with amcenestrant; (b) following step (a), administering amcenestrant to the individual and then determining a second ER activity score from a second sample from the individual at a second time point following the administration of amcenestrant; and (c) comparing the first ER activity score with the second ER activity score, wherein a decrease in the second ER activity score relative to the first ER activity score is predictive of target engagement of amcenestrant, wherein determining the first ER activity score and the second ER activity score comprises analyzing a panel of ER regulated genes, wherein the panel of ER regulated genes has 87 genes, and wherein the 87 genes comprise the following 21 upregulated genes: PTPRT, CAMK1D, BCAS1, ABCG1, KRT81, TLE2, SALL4, ITGB6, BBC3, IL1R1, CORO2A, GRM4, ATP6V0A4, MATN2, PPFIBP2, BMF, LOC283070, PSCA, BAK1, PLIN2, and SYNPO; and wherein the 87 genes comprise the following 66 downregulated genes: H19, MYBL1, MGP, SLC5A8, PKIB, PGR, TMPRSS3, IGSF1, COL21A1, FSIP1, KLHL4, EGR3, NPY1R, HIST1H3C, GRIK3, SCNN1B, FRK, PRSS23, SERPINA5, SFXN2, CAP2, HIST1H2BM, CDC45, WDR62, DSCC1, GJA1, FAM196A, NTRK2, RAD54L, SDK2, SLC4A10, HIST1H4D, HIST1H4C, RGS22, SYBU, CA8, DIAPH3, FHL2, HIST1H1B, KCNH1, RAD51AP1, FANCD2, SLC39A8, SKP2, HIST1H3B, TMEM164, AURKB, DEPTOR, XRCC2, C1QTNF6, ERCC6L, ORC1, HIST2H2AC, RRM2, EME1, HIST1H2BF, CLSPN, EXO1, SDC2, HIST1H3I, HIST2H2AB, HIST1H4B, ASCL1, ATAD5, HIST1H1D, and HIST1H2BH.

2. The method of claim 1, wherein a decrease in the second ER activity score relative to the first ER activity score is predictive of on-target activity of amcenestrant.

3. The method of claim 2, wherein the on-target activity of amcenestrant comprises ER degradation and ER inhibition.

4. The method of claim 1, wherein the analyzing of the panel of ER regulated genes at steps (a) and (b) comprises contacting, respectively, the first sample and the second sample from the individual with probes.

5. The method of claim 1, wherein the analyzing of the panel of ER regulated genes at steps (a) and (b) comprises detecting, respectively, the RNA expression level of each of the 87 genes in the first sample and the second sample from the individual.

6. The method of claim 1, wherein the analyzing of the panel of ER regulated genes at steps (a) and (b) comprises RNA sequencing.

7. The method of claim 1, wherein the individual has ER+ breast cancer.

8. The method of claim 1, wherein the individual has HER2− breast cancer.

9. The method of claim 1, wherein the individual has advanced or metastatic breast cancer.

10. The method of claim 1, wherein the first sample and the second sample are from a tumor biopsy.

11. The method of claim 1, wherein the first sample and the second sample are blood samples.

12. The method of claim 1, wherein the first sample and the second sample are serum samples.

13. The method of claim 10, wherein the tumor biopsy is a formalin-fixed tumor biopsy, a paraffin-embedded tumor biopsy, a formalin-fixed paraffin-embedded (FFPE) tumor biopsy, a fresh-frozen (FF) tumor biopsy, a frozen tumor biopsy, or a fresh tumor biopsy.

14. A kit comprising a set of detectably labeled probes for detecting expression of upregulated genes and downregulated genes, wherein the set of detectably labeled probes for detecting expression of upregulated genes and downregulated genes consists of 21 labeled probes to detect the upregulated genes PTPRT, CAMK1D, BCAS1, ABCG1, KRT81, TLE2, SALL4, ITGB6, BBC3, ILIR1, CORO2A, GRM4, ATP6V0A4, MATN2, PPFIBP2, BMF, LOC283070, PSCA, BAK1, PLIN2, and SYNPO; and 66 labeled probes to detect the downregulated genes H19, MYBL1, MGP, SLC5A8, PKIB, PGR, TMPRSS3, IGSF1, COL21A1, FSIP1, KLHL4, EGR3, NPY1R, HIST1H3C, GRIK3, SCNN1B, FRK, PRSS23, SERPINA5, SFXN2, CAP2, HIST1H2BM, CDC45, WDR62, DSCC1, GJA1, FAM196A, NTRK2, RAD54L, SDK2, SLC4A10, HIST1H4D, HIST1H4C, RGS22, SYBU, CA8, DIAPH3, FHL2, HIST1H1B, KCNH1, RAD51AP1, FANCD2, SLC39A8, SKP2, HIST1H3B, TMEM164, AURKB, DEPTOR, XRCC2, C1QTNF6, ERCC6L, ORC1, HIST2H2AC, RRM2, EME1, HIST1H2BF, CLSPN, EXO1, SDC2, HIST1H3I, HIST2H2AB, HIST1H4B, ASCL1, ATAD5, HIST1H1D, and HIST1H2BH.

* * * * *